US010487150B2

(12) United States Patent
Majeti et al.

(10) Patent No.: US 10,487,150 B2
(45) Date of Patent: Nov. 26, 2019

(54) SIRP ALPHA-ANTIBODY FUSION PROTEINS

(71) Applicant: The Board of Trustees of the Leland Stanford Junior University, Stanford, CA (US)

(72) Inventors: Ravindra Majeti, Palo Alto, CA (US); Emily Piccione Griffin, Belmont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/110,566

(22) Filed: Aug. 23, 2018

(65) Prior Publication Data
US 2018/0355053 A1 Dec. 13, 2018

Related U.S. Application Data

(62) Division of application No. 15/502,475, filed as application No. PCT/US2015/044304 on Aug. 7, 2015, now Pat. No. 10,087,257.

(60) Provisional application No. 62/035,273, filed on Aug. 8, 2014.

(51) Int. Cl.
| *C07K 16/30* | (2006.01) |
| *C07K 16/28* | (2006.01) |
| *C07K 14/705* | (2006.01) |
| *A61K 39/00* | (2006.01) |

(52) U.S. Cl.
CPC .... *C07K 16/2887* (2013.01); *C07K 14/70503* (2013.01); *C07K 14/70596* (2013.01); *C07K 16/2803* (2013.01); *C07K 16/2896* (2013.01); *C07K 16/3061* (2013.01); *A61K 2039/505* (2013.01); *C07K 2317/24* (2013.01); *C07K 2317/31* (2013.01); *C07K 2317/56* (2013.01); *C07K 2317/77* (2013.01); *C07K 2319/00* (2013.01); *C07K 2319/74* (2013.01)

(58) Field of Classification Search
None
See application file for complete search history.

(56) References Cited

U.S. PATENT DOCUMENTS

| 8,562,997 | B2 | 10/2013 | Jaiswal et al. | |
| 2009/0191202 | A1* | 7/2009 | Jamieson | G01N 33/5091 424/136.1 |
| 2014/0193408 | A1* | 7/2014 | Huber | C07K 14/70596 424/134.1 |

FOREIGN PATENT DOCUMENTS

| WO | 2011/034969 A1 | | 3/2011 |
| WO | WO 2011/034969 | * | 3/2011 |
| WO | 2011/076781 A1 | | 6/2011 |
| WO | 2013/109752 A1 | | 7/2013 |
| WO | WO 2013/109752 | * | 7/2013 |
| WO | 2014/087248 A2 | | 6/2014 |
| WO | 2014/121093 A1 | | 8/2014 |

OTHER PUBLICATIONS

Weiskopf et al (Science, 2013, 341:88-91).*
Guo et al. "Engineering Bispecific Macrophage-Enhancing Antibodies as New Cancer Immunotherapies", [online]. 2014 Scientific Meeting of Medical Fellows. May 19-21, 2014, [retrieved on Oct. 12, 2015]. Retrieved from the Internet: <URL: https://www.hhmi.org/sites/default/files/Programs/MedFellows/2014/2014-scientific-meeting-ofmedical-fellows-meeting-book.pdf>; pp. 1-61; p. 18, specific to Guo et al.
Piccione et al., "A Bispecific Antibody Targeting CD47 and CD20 Selectively Binds and Eliminates Dual Antigen Expressing Lymphoma Cells", mAbs, Jun. 17, 2015, pp. 946-956, vol. 7, No. 5, Taylor and Francis Online, Abingdon, United Kingdom.
Weiskopf et al., "Engineered SIRPα Variants as Immunotherapeutic Adjuvants to Anticancer Antibodies", Science, Jul. 5, 2013, pp. 88-91, vol. 341, Issue 6141, American Association for the Advancement of Science, Washington, D.C.
Barclay et al., "The Interaction Between Signal Regulatory Protein Alpha (SIRPα) and CD47: Structure, Function, and Therapeutic Target", Annual Review of Immunology, Mar. 21, 2014, pp. 25-50, vol. 32, No. 1, Annual Reviews, Palo Alto, CA.
Philippe et al., "Bispecific antibodies and trispecific immunocytokines for targeting the immune system against cancer: preparing for the future", Bio Drugs, Feb. 1, 2013, pp. 35-53, vol. 27, No. 1, German Cancer Research Center, Heidelberg, Germany.

* cited by examiner

*Primary Examiner* — Laura B Goddard
(74) *Attorney, Agent, or Firm* — Pamela J. Sherwood; Bozicevic, Field & Francis LLP

(57) ABSTRACT

SIRPabodies comprise an immunoglobulin variable region, which may specifically bind a tumor antigen, viral antigen, etc., fused to a sequence comprising a binding domain of SIRPα. The binding domain of SIRPα comprises at least the N-terminal Ig-like domain of SIRPα, and may further comprise additional SIRPα sequences. The SIRPabodies find use in therapeutic methods that benefit from the combined activity of blocking CD47 activity, and antibody targeting, e.g. in the treatment of cancer, etc. In some specific embodiments, the SIRPabody comprises anti-CD20 activity and a SIRPα binding domain; anti-CD99 and a SIRPα binding domain; or anti-TIM3 activity and a SIRPα binding domain.

15 Claims, 14 Drawing Sheets
(12 of 14 Drawing Sheet(s) Filed in Color)
Specification includes a Sequence Listing.

CD20-2GL-SIRPα
CD20-4GL-SIRPα

SIRPα-CD20

FIG. 8

| Antibody | $K_D$ (nM) |
|---|---|
| Anti-CD47 | 0.31 |
| SIRPα | 25.4 |
| CD20-2GL-SIRPα | 21.4 |
| CD20-4GL-SIRPα | 15.93 |
| SIRPα-CD20 | 6.39 |

SEQUENCE LISTING

<160> NUMBER OF SEQ ID NOS: 15

<210> SEQ ID NO 1
<211> LENGTH: 119
<212> TYPE: PRT
<213> ORGANISM: Homo sapiens

<400> SEQUENCE: 1

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 2
<211> LENGTH: 5
<212> TYPE: PRT
<213> ORGANISM: Homo sapiens

<400> SEQUENCE: 2

Gly Gly Gly Gly Ser
1               5

<210> SEQ ID NO 3
<211> LENGTH: 13
<212> TYPE: PRT
<213> ORGANISM: Homo sapiens

<400> SEQUENCE: 3

Ala Ser Thr Lys Gly Pro Ser Val Phe Pro Leu Ala Pro
1               5                   10

<210> SEQ ID NO 4
<211> LENGTH: 708
<212> TYPE: DNA
<213> ORGANISM: Homo sapiens
<220> FEATURE:
<221> NAME/KEY: CDS
<222> LOCATION: (1)...(708)

<400> SEQUENCE: 4 atg gat ttt cag gtg cag att atc agc ttc ctg cta atc agt gct tca    48
Met Asp Phe Gln Val Gln Ile Ile Ser Phe Leu Leu Ile Ser Ala Ser
1               5                   10                  15 gtc ata atg tcc aga gga caa att gtt ctc tcc cag tct cca gca atc    96
Val Ile Met Ser Arg Gly Gln Ile Val Leu Ser Gln Ser Pro Ala Ile
            20                  25                  30 ctg tct gca tct cca ggg gag aag gtc aca atg act tgc agg gcc agc   144
Leu Ser Ala Ser Pro Gly Glu Lys Val Thr Met Thr Cys Arg Ala Ser
        35                  40                  45

```
tca agt gta agt tac atc cac tgg ttc cag cag aag cca gga tcc tcc    192
Ser Ser Val Ser Tyr Ile His Trp Phe Gln Gln Lys Pro Gly Ser Ser
 50                  55                  60 ccc aaa ccc tgg att tat gcc aca tcc aac ctg gct tct gga gtc cct    240
Pro Lys Pro Trp Ile Tyr Ala Thr Ser Asn Leu Ala Ser Gly Val Pro
 65                  70                  75                  80 gtt cgc ttc agt ggc agt ggg tct ggg act tct tac tct ctc acc atc    288
Val Arg Phe Ser Gly Ser Gly Ser Gly Thr Ser Tyr Ser Leu Thr Ile
                 85                  90                  95 agc aga gtg gag gct gaa gat gct gcc act tat tac tgc cag cag tgg    336
Ser Arg Val Glu Ala Glu Asp Ala Ala Thr Tyr Tyr Cys Gln Gln Trp
            100                 105                 110 act agt aac cca ccc acg ttc gga ggg ggg acc aag ctg gaa atc aaa    384
Thr Ser Asn Pro Pro Thr Phe Gly Gly Gly Thr Lys Leu Glu Ile Lys
        115                 120                 125 cgt acg gtg gcg gcg cca tct gtc ttc atc ttc ccg cca tct gat gag    432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc    480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa    528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc    576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag    624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg    672
Lys His Lys Val Tyr Ala Cys Glu Val Thr His Gln Gly Leu Ser Ser
    210                 215                 220 ccc gtc aca aag agc ttc aac agg gga gag tgt tag                    708
Pro Val Thr Lys Ser Phe Asn Arg Gly Glu Cys *
225                 230                 235

<210> SEQ ID NO 5
<211> LENGTH: 235
<212> TYPE: PRT
<213> ORGANISM: Homo sapiens

<400> SEQUENCE: 5

Met Asp Phe Gln Val Gln Ile Ile Ser Phe Leu Leu Ile Ser Ala Ser
 1               5                  10                  15

Val Ile Met Ser Arg Gly Gln Ile Val Leu Ser Gln Ser Pro Ala Ile
             20                  25                  30

Leu Ser Ala Ser Pro Gly Glu Lys Val Thr Met Thr Cys Arg Ala Ser
         35                  40                  45

Ser Ser Val Ser Tyr Ile His Trp Phe Gln Gln Lys Pro Gly Ser Ser
     50                  55                  60

Pro Lys Pro Trp Ile Tyr Ala Thr Ser Asn Leu Ala Ser Gly Val Pro
 65                  70                  75                  80

Val Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125
```

```
Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 6
<211> LENGTH: 1800
<212> TYPE: DNA
<213> ORGANISM: Homo sapiens
<220> FEATURE:
<221> NAME/KEY: CDS
<222> LOCATION: (1)...(1800)

<400> SEQUENCE: 6 atg ggt tgg agc ctc atc ttg ctc ttc ctt gtc gct gtt gct acg cgt     48
Met Gly Trp Ser Leu Ile Leu Leu Phe Leu Val Ala Val Ala Thr Arg
1               5                   10                  15 gtc ctg tcc cag gta caa ctg cag cag cct ggg gct gag ctg gtg aag     96
Val Leu Ser Gln Val Gln Leu Gln Gln Pro Gly Ala Glu Leu Val Lys
            20                  25                  30 cct ggg gcc tca gtg aag atg tcc tgc aag gct tct ggc tac aca ttt    144
Pro Gly Ala Ser Val Lys Met Ser Cys Lys Ala Ser Gly Tyr Thr Phe
        35                  40                  45 acc agt tac aat atg cac tgg gta aaa cag aca cct ggt cgg ggc ctg    192
Thr Ser Tyr Asn Met His Trp Val Lys Gln Thr Pro Gly Arg Gly Leu
    50                  55                  60 gaa tgg att gga gct att tat ccc gga aat ggt gat act tcc tac aat    240
Glu Trp Ile Gly Ala Ile Tyr Pro Gly Asn Gly Asp Thr Ser Tyr Asn
65                  70                  75                  80 cag aag ttc aaa ggc aag gcc aca ttg act gca gac aaa tcc tcc agc    288
Gln Lys Phe Lys Gly Lys Ala Thr Leu Thr Ala Asp Lys Ser Ser Ser
                85                  90                  95 aca gcc tac atg cag ctc agc agc ctg aca tct gag gac tct gcg gtc    336
Thr Ala Tyr Met Gln Leu Ser Ser Leu Thr Ser Glu Asp Ser Ala Val
            100                 105                 110 tat tac tgt gca aga tcg act tac tac ggc ggt gac tgg tac ttc aat    384
Tyr Tyr Cys Ala Arg Ser Thr Tyr Tyr Gly Gly Asp Trp Tyr Phe Asn
        115                 120                 125 gtc tgg ggc gca ggg acc acg gtc acc gtc tct gca gcg agc acc aag    432
Val Trp Gly Ala Gly Thr Thr Val Thr Val Ser Ala Ala Ser Thr Lys
    130                 135                 140 ggc cca tcg gtc ttc ccc ctg gca ccc tcc tcc aag agc acc tct ggg    480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg    528
Gly Thr Ala Ala Leu Gly Cys Leu Val Lys Asp Tyr Phe Pro Glu Pro
                165                 170                 175 gtg acg gtg tcg tgg aac tca ggc gcc ctg acc agc ggc gtg cac acc    576
Val Thr Val Ser Trp Asn Ser Gly Ala Leu Thr Ser Gly Val His Thr
```

|     |     |     |     |     |     |     |     |     |     |     |     |     |     |     |     |      |
|---|---|---|---|---|---|---|---|---|---|---|---|---|---|---|---|---|
|     |     |     | 180 |     |     |     |     | 185 |     |     |     |     | 190 |     |     |      |
| ttc | ccg | gct | gtc | cta | cag | tcc | tca | gga | ctc | tac | tcc | ctc | agc | agc | gtg | 624  |
| Phe | Pro | Ala | Val | Leu | Gln | Ser | Ser | Gly | Leu | Tyr | Ser | Leu | Ser | Ser | Val |      |
|     |     | 195 |     |     |     |     | 200 |     |     |     |     | 205 |     |     |     |      |
| gtg | acc | gtg | ccc | tcc | agc | agc | ttg | ggc | acc | cag | acc | tac | atc | tgc | aac | 672  |
| Val | Thr | Val | Pro | Ser | Ser | Ser | Leu | Gly | Thr | Gln | Thr | Tyr | Ile | Cys | Asn |      |
|     | 210 |     |     |     |     | 215 |     |     |     |     | 220 |     |     |     |     |      |
| gtg | aat | cac | aag | ccc | agc | aac | acc | aag | gtg | gac | aag | aaa | gtt | gag | ccc | 720  |
| Val | Asn | His | Lys | Pro | Ser | Asn | Thr | Lys | Val | Asp | Lys | Lys | Val | Glu | Pro |      |
| 225 |     |     |     |     | 230 |     |     |     |     | 235 |     |     |     |     | 240 |      |
| aaa | tct | tgt | gac | aaa | act | cac | aca | tgc | cca | ccg | tgc | cca | gca | cct | gaa | 768  |
| Lys | Ser | Cys | Asp | Lys | Thr | His | Thr | Cys | Pro | Pro | Cys | Pro | Ala | Pro | Glu |      |
|     |     |     |     | 245 |     |     |     |     | 250 |     |     |     |     | 255 |     |      |
| ctc | ctg | ggg | gga | ccg | tca | gtc | ttc | ctc | ttc | ccc | cca | aaa | ccc | aag | gac | 816  |
| Leu | Leu | Gly | Gly | Pro | Ser | Val | Phe | Leu | Phe | Pro | Pro | Lys | Pro | Lys | Asp |      |
|     |     |     | 260 |     |     |     |     | 265 |     |     |     |     | 270 |     |     |      |
| acc | ctc | atg | atc | tcc | cgg | acc | cct | gag | gtc | aca | tgc | gtg | gtg | gtg | gac | 864  |
| Thr | Leu | Met | Ile | Ser | Arg | Thr | Pro | Glu | Val | Thr | Cys | Val | Val | Val | Asp |      |
|     |     | 275 |     |     |     |     | 280 |     |     |     |     | 285 |     |     |     |      |
| gtg | agc | cac | gaa | gac | cct | gag | gtc | aag | ttc | aac | tgg | tac | gtg | gac | ggc | 912  |
| Val | Ser | His | Glu | Asp | Pro | Glu | Val | Lys | Phe | Asn | Trp | Tyr | Val | Asp | Gly |      |
|     | 290 |     |     |     |     | 295 |     |     |     |     | 300 |     |     |     |     |      |
| gtg | gag | gtg | cat | aat | gcc | aag | aca | aag | ccg | cgg | gag | gag | cag | tac | aac | 960  |
| Val | Glu | Val | His | Asn | Ala | Lys | Thr | Lys | Pro | Arg | Glu | Glu | Gln | Tyr | Asn |      |
| 305 |     |     |     |     | 310 |     |     |     |     | 315 |     |     |     |     | 320 |      |
| agc | acg | tac | cgt | gtg | gtc | agc | gtc | ctc | acc | gtc | ctg | cac | cag | gac | tgg | 1008 |
| Ser | Thr | Tyr | Arg | Val | Val | Ser | Val | Leu | Thr | Val | Leu | His | Gln | Asp | Trp |      |
|     |     |     |     | 325 |     |     |     |     | 330 |     |     |     |     | 335 |     |      |
| ctg | aat | ggc | aag | gag | tac | aag | tgc | aag | gtc | tcc | aac | aaa | gcc | ctc | cca | 1056 |
| Leu | Asn | Gly | Lys | Glu | Tyr | Lys | Cys | Lys | Val | Ser | Asn | Lys | Ala | Leu | Pro |      |
|     |     |     | 340 |     |     |     |     | 345 |     |     |     |     | 350 |     |     |      |
| gcc | ccc | atc | gag | aaa | acc | atc | tcc | aaa | gcc | aaa | ggg | cag | ccc | cga | gaa | 1104 |
| Ala | Pro | Ile | Glu | Lys | Thr | Ile | Ser | Lys | Ala | Lys | Gly | Gln | Pro | Arg | Glu |      |
|     |     | 355 |     |     |     |     | 360 |     |     |     |     | 365 |     |     |     |      |
| cca | cag | gtg | tac | acc | ctg | ccc | cca | tcc | cgg | gat | gag | ctg | acc | aag | aac | 1152 |
| Pro | Gln | Val | Tyr | Thr | Leu | Pro | Pro | Ser | Arg | Asp | Glu | Leu | Thr | Lys | Asn |      |
|     | 370 |     |     |     |     | 375 |     |     |     |     | 380 |     |     |     |     |      |
| cag | gtc | agc | ctg | acc | tgc | ctg | gtc | aaa | ggc | ttc | tat | ccc | agc | gac | atc | 1200 |
| Gln | Val | Ser | Leu | Thr | Cys | Leu | Val | Lys | Gly | Phe | Tyr | Pro | Ser | Asp | Ile |      |
| 385 |     |     |     |     | 390 |     |     |     |     | 395 |     |     |     |     | 400 |      |
| gcc | gtg | gag | tgg | gag | agc | aat | ggg | cag | ccg | gag | aac | aac | tac | aag | acc | 1248 |
| Ala | Val | Glu | Trp | Glu | Ser | Asn | Gly | Gln | Pro | Glu | Asn | Asn | Tyr | Lys | Thr |      |
|     |     |     |     | 405 |     |     |     |     | 410 |     |     |     |     | 415 |     |      |
| acg | cct | ccc | gtg | ctg | gac | tcc | gac | ggc | tcc | ttc | ttc | ctc | tac | agc | aag | 1296 |
| Thr | Pro | Pro | Val | Leu | Asp | Ser | Asp | Gly | Ser | Phe | Phe | Leu | Tyr | Ser | Lys |      |
|     |     |     | 420 |     |     |     |     | 425 |     |     |     |     | 430 |     |     |      |
| ctc | acc | gtg | gac | aag | agc | agg | tgg | cag | cag | ggg | aac | gtc | ttc | tca | tgc | 1344 |
| Leu | Thr | Val | Asp | Lys | Ser | Arg | Trp | Gln | Gln | Gly | Asn | Val | Phe | Ser | Cys |      |
|     |     | 435 |     |     |     |     | 440 |     |     |     |     | 445 |     |     |     |      |
| tcc | gtg | atg | cat | gag | gct | ctg | cac | aac | cac | tac | acg | cag | aag | agc | ctc | 1392 |
| Ser | Val | Met | His | Glu | Ala | Leu | His | Asn | His | Tyr | Thr | Gln | Lys | Ser | Leu |      |
|     | 450 |     |     |     |     | 455 |     |     |     |     | 460 |     |     |     |     |      |
| tcc | ctg | tct | ccg | ggt | aaa | ggt | ggc | ggt | ggc | tcg | ggc | ggt | ggt | ggg | tcg | 1440 |
| Ser | Leu | Ser | Pro | Gly | Lys | Gly | Gly | Gly | Gly | Ser | Gly | Gly | Gly | Gly | Ser |      |
| 465 |     |     |     |     | 470 |     |     |     |     | 475 |     |     |     |     | 480 |      |
| gag | gag | gag | ctg | cag | gtg | att | cag | cct | gac | aag | tcc | gtg | ttg | gtt | gca | 1488 |
| Glu | Glu | Glu | Leu | Gln | Val | Ile | Gln | Pro | Asp | Lys | Ser | Val | Leu | Val | Ala |      |
|     |     |     |     | 485 |     |     |     |     | 490 |     |     |     |     | 495 |     |      |
| gct | gga | gag | aca | gcc | act | ctg | cgc | tgc | act | gcg | acc | tct | ctg | atc | cct | 1536 |

```
                Ala Gly Glu Thr Ala Thr Leu Arg Cys Thr Ala Thr Ser Leu Ile Pro
                                500                 505                 510 gtg ggg ccc atc cag tgg ttc aga gga gct gga cca ggc cgg gaa tta              1584
Val Gly Pro Ile Gln Trp Phe Arg Gly Ala Gly Pro Gly Arg Glu Leu
                515                 520                 525 atc tac aat caa aaa gaa ggc cac ttc ccc cgg gta aca act gtt tca              1632
Ile Tyr Asn Gln Lys Glu Gly His Phe Pro Arg Val Thr Thr Val Ser
        530                 535                 540 gac ctc aca aag aga aac aac atg gac ttt tcc atc cgc atc ggt aac              1680
Asp Leu Thr Lys Arg Asn Asn Met Asp Phe Ser Ile Arg Ile Gly Asn
545                 550                 555                 560 atc acc cca gca gat gcc ggc acc tac tac tgt gtg aag ttc cgg aaa              1728
Ile Thr Pro Ala Asp Ala Gly Thr Tyr Tyr Cys Val Lys Phe Arg Lys
                565                 570                 575 ggg agc ccc gat gac gtg gag ttt aag tct gga gca ggc act gag ctg              1776
Gly Ser Pro Asp Asp Val Glu Phe Lys Ser Gly Ala Gly Thr Glu Leu
                580                 585                 590 tct gtg cgc gcc aaa ccc tct tga                                              1800
Ser Val Arg Ala Lys Pro Ser *
        595

<210> SEQ ID NO 7
<211> LENGTH: 599
<212> TYPE: PRT
<213> ORGANISM: Homo sapiens

<400> SEQUENCE: 7

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240
```

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Gly Gly Gly Ser Gly Gly Gly Gly Ser
465                 470                 475                 480

Glu Glu Glu Leu Gln Val Ile Gln Pro Asp Lys Ser Val Leu Val Ala
                485                 490                 495

Ala Gly Glu Thr Ala Thr Leu Arg Cys Thr Ala Thr Ser Leu Ile Pro
            500                 505                 510

Val Gly Pro Ile Gln Trp Phe Arg Gly Ala Gly Pro Gly Arg Glu Leu
        515                 520                 525

Ile Tyr Asn Gln Lys Glu Gly His Phe Pro Arg Val Thr Thr Val Ser
    530                 535                 540

Asp Leu Thr Lys Arg Asn Asn Met Asp Phe Ser Ile Arg Ile Gly Asn
545                 550                 555                 560

Ile Thr Pro Ala Asp Ala Gly Thr Tyr Tyr Cys Val Lys Phe Arg Lys
                565                 570                 575

Gly Ser Pro Asp Asp Val Glu Phe Lys Ser Gly Ala Gly Thr Glu Leu
            580                 585                 590

Ser Val Arg Ala Lys Pro Ser
        595

<210> SEQ ID NO 8
<211> LENGTH: 1803
<212> TYPE: DNA
<213> ORGANISM: Homo sapiens
<220> FEATURE:
<221> NAME/KEY: CDS
<222> LOCATION: (1)...(1803)

```
<400> SEQUENCE: 8 atg agg gct tgg atc ttc ttt ctg ctc tgc ctg gcc ggg cgc gcc ttg      48
Met Arg Ala Trp Ile Phe Phe Leu Leu Cys Leu Ala Gly Arg Ala Leu
 1               5                  10                  15 gcc gag gag gag ctg cag gtg att cag cct gac aag tcc gtg ttg gtt      96
Ala Glu Glu Glu Leu Gln Val Ile Gln Pro Asp Lys Ser Val Leu Val
                20                  25                  30 gca gct gga gag aca gcc act ctg cgc tgc act gcg acc tct ctg atc     144
Ala Ala Gly Glu Thr Ala Thr Leu Arg Cys Thr Ala Thr Ser Leu Ile
             35                  40                  45 cct gtg ggg ccc atc cag tgg ttc aga gga gct gga cca ggc cgg gaa     192
Pro Val Gly Pro Ile Gln Trp Phe Arg Gly Ala Gly Pro Gly Arg Glu
         50                  55                  60 tta atc tac aat caa aaa gaa ggc cac ttc ccc cgg gta aca act gtt     240
Leu Ile Tyr Asn Gln Lys Glu Gly His Phe Pro Arg Val Thr Thr Val
 65                  70                  75                  80 tca gac ctc aca aag aga aac aac atg gac ttt tcc atc cgc atc ggt     288
Ser Asp Leu Thr Lys Arg Asn Asn Met Asp Phe Ser Ile Arg Ile Gly
                 85                  90                  95 aac atc acc cca gca gat gcc ggc acc tac tac tgt gtg aag ttc cgg     336
Asn Ile Thr Pro Ala Asp Ala Gly Thr Tyr Tyr Cys Val Lys Phe Arg
            100                 105                 110 aaa ggg agc ccc gat gac gtg gag ttt aag tct gga gca ggc act gag     384
Lys Gly Ser Pro Asp Asp Val Glu Phe Lys Ser Gly Ala Gly Thr Glu
        115                 120                 125 ctg tct gtg cgc gcc aaa ccc tct gcg agc acc aag ggc cca tcg gtc     432
Leu Ser Val Arg Ala Lys Pro Ser Ala Ser Thr Lys Gly Pro Ser Val
    130                 135                 140 ttc ccc ctg gca ccc cag gta caa ctg cag cag cct ggg gct gag ctg     480
Phe Pro Leu Ala Pro Gln Val Gln Leu Gln Gln Pro Gly Ala Glu Leu
145                 150                 155                 160 gtg aag cct ggg gcc tca gtg aag atg tcc tgc aag gct tct ggc tac     528
Val Lys Pro Gly Ala Ser Val Lys Met Ser Cys Lys Ala Ser Gly Tyr
                165                 170                 175 aca ttt acc agt tac aat atg cac tgg gta aaa cag aca cct ggt cgg     576
Thr Phe Thr Ser Tyr Asn Met His Trp Val Lys Gln Thr Pro Gly Arg
            180                 185                 190 ggc ctg gaa tgg att gga gct att tat ccc gga aat ggt gat act tcc     624
Gly Leu Glu Trp Ile Gly Ala Ile Tyr Pro Gly Asn Gly Asp Thr Ser
        195                 200                 205 tac aat cag aag ttc aaa ggc aag gcc aca ttg act gca gac aaa tcc     672
Tyr Asn Gln Lys Phe Lys Gly Lys Ala Thr Leu Thr Ala Asp Lys Ser
    210                 215                 220 tcc agc aca gcc tac atg cag ctc agc agc ctg aca tct gag gac tct     720
Ser Ser Thr Ala Tyr Met Gln Leu Ser Ser Leu Thr Ser Glu Asp Ser
225                 230                 235                 240 gcg gtc tat tac tgt gca aga tcg act tac tac ggc ggt gac tgg tac     768
Ala Val Tyr Tyr Cys Ala Arg Ser Thr Tyr Tyr Gly Gly Asp Trp Tyr
                245                 250                 255 ttc aat gtc tgg ggc gca ggg acc acg gtc acc gtc tct gca gct agc     816
Phe Asn Val Trp Gly Ala Gly Thr Thr Val Thr Val Ser Ala Ala Ser
            260                 265                 270 acc aag ggc cca tcg gtc ttc ccc ctg gca ccc tcc tcc aag agc acc     864
Thr Lys Gly Pro Ser Val Phe Pro Leu Ala Pro Ser Ser Lys Ser Thr
        275                 280                 285 tct ggg ggc aca gcg gcc ctg ggc tgc ctg gtc aag gac tac ttc ccc     912
Ser Gly Gly Thr Ala Ala Leu Gly Cys Leu Val Lys Asp Tyr Phe Pro
    290                 295                 300 gaa ccg gtg acg gtg tcg tgg aac tca ggc gcc ctg acc agc ggc gtg     960
Glu Pro Val Thr Val Ser Trp Asn Ser Gly Ala Leu Thr Ser Gly Val
```

```
Glu Pro Val Thr Val Ser Trp Asn Ser Gly Ala Leu Thr Ser Gly Val
305                 310                 315                 320 cac acc ttc ccg gct gtc cta cag tcc tca gga ctc tac tcc ctc agc       1008
His Thr Phe Pro Ala Val Leu Gln Ser Ser Gly Leu Tyr Ser Leu Ser
                325                 330                 335 agc gtg gtg acc gtg ccc tcc agc agc ttg ggc acc cag acc tac atc       1056
Ser Val Val Thr Val Pro Ser Ser Ser Leu Gly Thr Gln Thr Tyr Ile
                340                 345                 350 tgc aac gtg aat cac aag ccc agc aac acc aag gtg gac aag aaa gtt       1104
Cys Asn Val Asn His Lys Pro Ser Asn Thr Lys Val Asp Lys Lys Val
                355                 360                 365 gag ccc aaa tct tgt gac aaa act cac aca tgc cca ccg tgc cca gca       1152
Glu Pro Lys Ser Cys Asp Lys Thr His Thr Cys Pro Pro Cys Pro Ala
370                 375                 380 cct gaa ctc ctg ggg gga ccg tca gtc ttt ctc ttc ccc cca aaa ccc       1200
Pro Glu Leu Leu Gly Gly Pro Ser Val Phe Leu Phe Pro Pro Lys Pro
385                 390                 395                 400 aag gac acc ctc atg atc tcc cgg acc cct gag gtc aca tgc gtg gtg       1248
Lys Asp Thr Leu Met Ile Ser Arg Thr Pro Glu Val Thr Cys Val Val
                405                 410                 415 gtg gac gtg agc cac gaa gac cct gag gtc aag ttc aac tgg tac gtg       1296
Val Asp Val Ser His Glu Asp Pro Glu Val Lys Phe Asn Trp Tyr Val
                420                 425                 430 gac ggc gtg gag gtg cat aat gcc aag aca aag ccg cgg gag gag cag       1344
Asp Gly Val Glu Val His Asn Ala Lys Thr Lys Pro Arg Glu Glu Gln
                435                 440                 445 tac aac agc acg tac cgt gtg gtc agc gtc ctc acc gtc ctg cac cag       1392
Tyr Asn Ser Thr Tyr Arg Val Val Ser Val Leu Thr Val Leu His Gln
450                 455                 460 gac tgg ctg aat ggc aag gag tac aag tgc aag gtc tcc aac aaa gcc       1440
Asp Trp Leu Asn Gly Lys Glu Tyr Lys Cys Lys Val Ser Asn Lys Ala
465                 470                 475                 480 ctc cca gcc ccc atc gag aaa acc atc tcc aaa gcc aaa ggg cag ccc       1488
Leu Pro Ala Pro Ile Glu Lys Thr Ile Ser Lys Ala Lys Gly Gln Pro
                485                 490                 495 cga gaa cca cag gtg tac acc ctg ccc cca tcc cgg gat gag ctg acc       1536
Arg Glu Pro Gln Val Tyr Thr Leu Pro Pro Ser Arg Asp Glu Leu Thr
                500                 505                 510 aag aac cag gtc agc ctg acc tgc ctg gtc aaa ggc ttc tat ccc agc       1584
Lys Asn Gln Val Ser Leu Thr Cys Leu Val Lys Gly Phe Tyr Pro Ser
                515                 520                 525 gac atc gcc gtg gag tgg gag agc aat ggg cag ccg gag aac aac tac       1632
Asp Ile Ala Val Glu Trp Glu Ser Asn Gly Gln Pro Glu Asn Asn Tyr
                530                 535                 540 aag acc acg cct ccc gtg ctg gac tcc gac ggc tcc ttc ttc ctc tat       1680
Lys Thr Thr Pro Pro Val Leu Asp Ser Asp Gly Ser Phe Phe Leu Tyr
545                 550                 555                 560 agc aag ctc acc gtg gac aag agc agg tgg cag cag ggg aac gtc ttc       1728
Ser Lys Leu Thr Val Asp Lys Ser Arg Trp Gln Gln Gly Asn Val Phe
                565                 570                 575 tca tgc tcc gtg atg cat gag gct ctg cac aac cac tac acg cag aag       1776
Ser Cys Ser Val Met His Glu Ala Leu His Asn His Tyr Thr Gln Lys
                580                 585                 590 agc ctc tcc ctg tct ccg ggt aaa tga                                   1803
Ser Leu Ser Leu Ser Pro Gly Lys *
                595                 600

<210> SEQ ID NO 9
<211> LENGTH: 600
<212> TYPE: PRT
```

<213> ORGANISM: Homo sapiens

<400> SEQUENCE: 9

Met Arg Ala Trp Ile Phe Phe Leu Leu Cys Leu Ala Gly Arg Ala Leu
1               5                   10                  15

Ala Glu Glu Leu Gln Val Ile Gln Pro Asp Lys Ser Val Leu Val
            20                  25                  30

Ala Ala Gly Glu Thr Ala Thr Leu Arg Cys Thr Ala Thr Ser Leu Ile
            35                  40                  45

Pro Val Gly Pro Ile Gln Trp Phe Arg Gly Ala Gly Pro Gly Arg Glu
    50                  55                  60

Leu Ile Tyr Asn Gln Lys Glu Gly His Phe Pro Arg Val Thr Thr Val
65                  70                  75                  80

Ser Asp Leu Thr Lys Arg Asn Asn Met Asp Phe Ser Ile Arg Ile Gly
                85                  90                  95

Asn Ile Thr Pro Ala Asp Ala Gly Thr Tyr Tyr Cys Val Lys Phe Arg
            100                 105                 110

Lys Gly Ser Pro Asp Asp Val Glu Phe Lys Ser Gly Ala Gly Thr Glu
            115                 120                 125

Leu Ser Val Arg Ala Lys Pro Ser Ala Ser Thr Lys Gly Pro Ser Val
    130                 135                 140

Phe Pro Leu Ala Pro Gln Val Gln Leu Gln Gln Pro Gly Ala Glu Leu
145                 150                 155                 160

Val Lys Pro Gly Ala Ser Val Lys Met Ser Cys Lys Ala Ser Gly Tyr
                165                 170                 175

Thr Phe Thr Ser Tyr Asn Met His Trp Val Lys Gln Thr Pro Gly Arg
            180                 185                 190

Gly Leu Glu Trp Ile Gly Ala Ile Tyr Pro Gly Asn Gly Asp Thr Ser
    195                 200                 205

Tyr Asn Gln Lys Phe Lys Gly Lys Ala Thr Leu Thr Ala Asp Lys Ser
210                 215                 220

Ser Ser Thr Ala Tyr Met Gln Leu Ser Ser Leu Thr Ser Glu Asp Ser
225                 230                 235                 240

Ala Val Tyr Tyr Cys Ala Arg Ser Thr Tyr Tyr Gly Gly Asp Trp Tyr
                245                 250                 255

Phe Asn Val Trp Gly Ala Gly Thr Thr Val Thr Val Ser Ala Ala Ser
            260                 265                 270

Thr Lys Gly Pro Ser Val Phe Pro Leu Ala Pro Ser Ser Lys Ser Thr
    275                 280                 285

Ser Gly Gly Thr Ala Ala Leu Gly Cys Leu Val Lys Asp Tyr Phe Pro
290                 295                 300

Glu Pro Val Thr Val Ser Trp Asn Ser Gly Ala Leu Thr Ser Gly Val
305                 310                 315                 320

His Thr Phe Pro Ala Val Leu Gln Ser Ser Gly Leu Tyr Ser Leu Ser
                325                 330                 335

Ser Val Val Thr Val Pro Ser Ser Ser Leu Gly Thr Gln Thr Tyr Ile
            340                 345                 350

Cys Asn Val Asn His Lys Pro Ser Asn Thr Lys Val Asp Lys Lys Val
    355                 360                 365

Glu Pro Lys Ser Cys Asp Lys Thr His Thr Cys Pro Pro Cys Pro Ala
370                 375                 380

Pro Glu Leu Leu Gly Gly Pro Ser Val Phe Leu Phe Pro Pro Lys Pro
385                 390                 395                 400

-continued

| | | | | | | | | | | |
|---|---|---|---|---|---|---|---|---|---|---|
|Lys|Asp|Thr|Leu|Met|Ile|Ser|Arg|Thr|Pro|Glu|Val|Thr|Cys|Val|Val|
| | | | |405| | | |410| | | |415| | | |

Val Asp Val Ser His Glu Asp Pro Glu Val Lys Phe Asn Trp Tyr Val
            420                 425                 430

Asp Gly Val Glu Val His Asn Ala Lys Thr Lys Pro Arg Glu Glu Gln
            435                 440                 445

Tyr Asn Ser Thr Tyr Arg Val Val Ser Val Leu Thr Val Leu His Gln
450                 455                 460

Asp Trp Leu Asn Gly Lys Glu Tyr Lys Cys Lys Val Ser Asn Lys Ala
465                 470                 475                 480

Leu Pro Ala Pro Ile Glu Lys Thr Ile Ser Lys Ala Lys Gly Gln Pro
            485                 490                 495

Arg Glu Pro Gln Val Tyr Thr Leu Pro Pro Ser Arg Asp Glu Leu Thr
            500                 505                 510

Lys Asn Gln Val Ser Leu Thr Cys Leu Val Lys Gly Phe Tyr Pro Ser
            515                 520                 525

Asp Ile Ala Val Glu Trp Glu Ser Asn Gly Gln Pro Glu Asn Asn Tyr
530                 535                 540

Lys Thr Thr Pro Pro Val Leu Asp Ser Asp Gly Ser Phe Phe Leu Tyr
545                 550                 555                 560

Ser Lys Leu Thr Val Asp Lys Ser Arg Trp Gln Gln Gly Asn Val Phe
            565                 570                 575

Ser Cys Ser Val Met His Glu Ala Leu His Asn His Tyr Thr Gln Lys
            580                 585                 590

Ser Leu Ser Leu Ser Pro Gly Lys
            595                 600

<210> SEQ ID NO 10
<211> LENGTH: 1830
<212> TYPE: DNA
<213> ORGANISM: Homo sapiens
<220> FEATURE:
<221> NAME/KEY: CDS
<222> LOCATION: (1)...(1830)

<400> SEQUENCE: 10 atg ggt tgg agc ctc atc ttg ctc ttc ctt gtc gct gtt gct acg cgt       48
Met Gly Trp Ser Leu Ile Leu Leu Phe Leu Val Ala Val Ala Thr Arg
1               5                   10                  15 gtc ctg tcc cag gta caa ctg cag cag cct ggg gct gag ctg gtg aag       96
Val Leu Ser Gln Val Gln Leu Gln Gln Pro Gly Ala Glu Leu Val Lys
            20                  25                  30 cct ggg gcc tca gtg aag atg tcc tgc aag gct tct ggc tac aca ttt      144
Pro Gly Ala Ser Val Lys Met Ser Cys Lys Ala Ser Gly Tyr Thr Phe
        35                  40                  45 acc agt tac aat atg cac tgg gta aaa cag aca cct ggt cgg ggc ctg      192
Thr Ser Tyr Asn Met His Trp Val Lys Gln Thr Pro Gly Arg Gly Leu
    50                  55                  60 gaa tgg att gga gct att tat ccc gga aat ggt gat act tcc tac aat      240
Glu Trp Ile Gly Ala Ile Tyr Pro Gly Asn Gly Asp Thr Ser Tyr Asn
65                  70                  75                  80 cag aag ttc aaa ggc aag gcc aca ttg act gca gac aaa tcc tcc agc      288
Gln Lys Phe Lys Gly Lys Ala Thr Leu Thr Ala Asp Lys Ser Ser Ser
                85                  90                  95 aca gcc tac atg cag ctc agc agc ctg aca tct gag gac tct gcg gtc      336
Thr Ala Tyr Met Gln Leu Ser Ser Leu Thr Ser Glu Asp Ser Ala Val
            100                 105                 110 tat tac tgt gca aga tcg act tac tac ggc ggt gac tgg tac ttc aat      384

-continued

```
                Tyr Tyr Cys Ala Arg Ser Thr Tyr Gly Gly Asp Trp Tyr Phe Asn
                        115                 120                 125 gtc tgg ggc gca ggg acc acg gtc acc gtc tct gca gcg agc acc aag           432
Val Trp Gly Ala Gly Thr Thr Val Thr Val Ser Ala Ala Ser Thr Lys
130                 135                 140 ggc cca tcg gtc ttc ccc ctg gca ccc tcc tcc aag agc acc tct ggg           480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg           528
Gly Thr Ala Ala Leu Gly Cys Leu Val Lys Asp Tyr Phe Pro Glu Pro
                165                 170                 175 gtg acg gtg tcg tgg aac tca ggc gcc ctg acc agc ggc gtg cac acc           576
Val Thr Val Ser Trp Asn Ser Gly Ala Leu Thr Ser Gly Val His Thr
                180                 185                 190 ttc ccg gct gtc cta cag tcc tca gga ctc tac tcc ctc agc agc gtg           624
Phe Pro Ala Val Leu Gln Ser Ser Gly Leu Tyr Ser Leu Ser Ser Val
                195                 200                 205 gtg acc gtg ccc tcc agc agc ttg ggc acc cag acc tac atc tgc aac           672
Val Thr Val Pro Ser Ser Ser Leu Gly Thr Gln Thr Tyr Ile Cys Asn
210                 215                 220 gtg aat cac aag ccc agc aac acc aag gtg gac aag aaa gtt gag ccc           720
Val Asn His Lys Pro Ser Asn Thr Lys Val Asp Lys Lys Val Glu Pro
225                 230                 235                 240 aaa tct tgt gac aaa act cac aca tgc cca ccg tgc cca gca cct gaa           768
Lys Ser Cys Asp Lys Thr His Thr Cys Pro Pro Cys Pro Ala Pro Glu
                245                 250                 255 ctc ctg ggg gga ccg tca gtc ttt ctc ttc ccc cca aaa ccc aag gac           816
Leu Leu Gly Gly Pro Ser Val Phe Leu Phe Pro Pro Lys Pro Lys Asp
                260                 265                 270 acc ctc atg atc tcc cgg acc cct gag gtc aca tgc gtg gtg gtg gac           864
Thr Leu Met Ile Ser Arg Thr Pro Glu Val Thr Cys Val Val Val Asp
                275                 280                 285 gtg agc cac gaa gac cct gag gtc aag ttc aac tgg tac gtg gac ggc           912
Val Ser His Glu Asp Pro Glu Val Lys Phe Asn Trp Tyr Val Asp Gly
290                 295                 300 gtg gag gtg cat aat gcc aag aca aag ccg cgg gag gag cag tac aac           960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg          1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca          1056
Leu Asn Gly Lys Glu Tyr Lys Cys Lys Val Ser Asn Lys Ala Leu Pro
                340                 345                 350 gcc ccc atc gag aaa acc atc tcc aaa gcc aaa ggg cag ccc cga gaa          1104
Ala Pro Ile Glu Lys Thr Ile Ser Lys Ala Lys Gly Gln Pro Arg Glu
                355                 360                 365 cca cag gtg tac acc ctg ccc cca tcc cgg gat gag ctg acc aag aac          1152
Pro Gln Val Tyr Thr Leu Pro Pro Ser Arg Asp Glu Leu Thr Lys Asn
370                 375                 380 cag gtc agc ctg acc tgc ctg gtc aaa ggc ttc tat ccc agc gac atc          1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc          1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tat agc aag          1296
Thr Pro Pro Val Leu Asp Ser Asp Gly Ser Phe Phe Leu Tyr Ser Lys
                420                 425                 430
```

| | | | | | | | | | | | | | | | | |
|---|---|---|---|---|---|---|---|---|---|---|---|---|---|---|---|---|
| ctc | acc | gtg | gac | aag | agc | agg | tgg | cag | cag | ggg | aac | gtc | ttc | tca | tgc | 1344 |
| Leu | Thr | Val | Asp | Lys | Ser | Arg | Trp | Gln | Gln | Gly | Asn | Val | Phe | Ser | Cys | |
| | | | 435 | | | | | 440 | | | | | 445 | | | |
| tcc | gtg | atg | cat | gag | gct | ctg | cac | aac | cac | tac | acg | cag | aag | agc | ctc | 1392 |
| Ser | Val | Met | His | Glu | Ala | Leu | His | Asn | His | Tyr | Thr | Gln | Lys | Ser | Leu | |
| | | 450 | | | | | 455 | | | | | 460 | | | | |
| tcc | ctg | tct | ccg | ggt | aaa | ggt | ggc | ggt | tcg | ggc | ggt | ggt | ggg | tcg | | 1440 |
| Ser | Leu | Ser | Pro | Gly | Lys | Gly | Gly | Gly | Ser | Gly | Gly | Gly | Gly | Ser | | |
| 465 | | | | 470 | | | | | 475 | | | | | 480 | | |
| ggt | ggc | ggc | gga | tct | ggc | ggt | ggt | tct | gag | gag | gag | ctg | cag | gtg | | 1488 |
| Gly | Gly | Gly | Gly | Ser | Gly | Gly | Gly | Ser | Glu | Glu | Glu | Leu | Gln | Val | | |
| | | | | 485 | | | | 490 | | | | | 495 | | | |
| att | cag | cct | gac | aag | tcc | gtg | ttg | gtt | gca | gct | gga | gag | aca | gcc | act | 1536 |
| Ile | Gln | Pro | Asp | Lys | Ser | Val | Leu | Val | Ala | Ala | Gly | Glu | Thr | Ala | Thr | |
| | | | 500 | | | | | 505 | | | | | 510 | | | |
| ctg | cgc | tgc | act | gcg | acc | tct | ctg | atc | cct | gtg | ggg | ccc | atc | cag | tgg | 1584 |
| Leu | Arg | Cys | Thr | Ala | Thr | Ser | Leu | Ile | Pro | Val | Gly | Pro | Ile | Gln | Trp | |
| | | | 515 | | | | | 520 | | | | | 525 | | | |
| ttc | aga | gga | gct | gga | cca | ggc | cgg | gaa | tta | atc | tac | aat | caa | aaa | gaa | 1632 |
| Phe | Arg | Gly | Ala | Gly | Pro | Gly | Arg | Glu | Leu | Ile | Tyr | Asn | Gln | Lys | Glu | |
| | 530 | | | | | 535 | | | | | 540 | | | | | |
| ggc | cac | ttc | ccc | cgg | gta | aca | act | gtt | tca | gac | ctc | aca | aag | aga | aac | 1680 |
| Gly | His | Phe | Pro | Arg | Val | Thr | Thr | Val | Ser | Asp | Leu | Thr | Lys | Arg | Asn | |
| 545 | | | | | 550 | | | | | 555 | | | | | 560 | |
| aac | atg | gac | ttt | tcc | atc | cgc | atc | ggt | aac | atc | acc | cca | gca | gat | gcc | 1728 |
| Asn | Met | Asp | Phe | Ser | Ile | Arg | Ile | Gly | Asn | Ile | Thr | Pro | Ala | Asp | Ala | |
| | | | | 565 | | | | 570 | | | | | 575 | | | |
| ggc | acc | tac | tac | tgt | gtg | aag | ttc | cgg | aaa | ggg | agc | ccc | gat | gac | gtg | 1776 |
| Gly | Thr | Tyr | Tyr | Cys | Val | Lys | Phe | Arg | Lys | Gly | Ser | Pro | Asp | Asp | Val | |
| | | | 580 | | | | | 585 | | | | | 590 | | | |
| gag | ttt | aag | tct | gga | gca | ggc | act | gag | ctg | tct | gtg | cgc | gcc | aaa | ccc | 1824 |
| Glu | Phe | Lys | Ser | Gly | Ala | Gly | Thr | Glu | Leu | Ser | Val | Arg | Ala | Lys | Pro | |
| | | | 595 | | | | 600 | | | | | 605 | | | | |
| tct | tga | | | | | | | | | | | | | | | 1830 |
| Ser | * | | | | | | | | | | | | | | | |

<210> SEQ ID NO 11
<211> LENGTH: 609
<212> TYPE: PRT
<213> ORGANISM: Homo sapiens

<400> SEQUENCE: 11

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys

```
            130                 135                 140
Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                    180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
            450                 455                 460

Ser Leu Ser Pro Gly Lys Gly Gly Gly Ser Gly Gly Gly Gly Ser
465                 470                 475                 480

Gly Gly Gly Gly Ser Gly Gly Gly Ser Glu Glu Glu Leu Gln Val
                485                 490                 495

Ile Gln Pro Asp Lys Ser Val Leu Val Ala Ala Gly Glu Thr Ala Thr
                500                 505                 510

Leu Arg Cys Thr Ala Thr Ser Leu Ile Pro Val Gly Pro Ile Gln Trp
                515                 520                 525

Phe Arg Gly Ala Gly Pro Gly Arg Glu Leu Ile Tyr Asn Gln Lys Glu
            530                 535                 540

Gly His Phe Pro Arg Val Thr Thr Val Ser Asp Leu Thr Lys Arg Asn
545                 550                 555                 560
```

```
Asn Met Asp Phe Ser Ile Arg Ile Gly Asn Ile Thr Pro Ala Asp Ala
            565                 570                 575

Gly Thr Tyr Tyr Cys Val Lys Phe Arg Lys Gly Ser Pro Asp Asp Val
        580                 585                 590

Glu Phe Lys Ser Gly Ala Gly Thr Glu Leu Ser Val Arg Ala Lys Pro
        595                 600                 605

Ser

<210> SEQ ID NO 12
<211> LENGTH: 711
<212> TYPE: DNA
<213> ORGANISM: Homo sapiens
<220> FEATURE:
<221> NAME/KEY: CDS
<222> LOCATION: (1)...(711)

<400> SEQUENCE: 12
```

| | | | | | | | | | | | | | | | | |
|---|---|---|---|---|---|---|---|---|---|---|---|---|---|---|---|---|
| atg | agg | gct | tgg | atc | ttc | ttt | ctg | ctc | tgc | ctg | gcc | ggg | cgc | gcc | ttg | 48 |
| Met | Arg | Ala | Trp | Ile | Phe | Phe | Leu | Leu | Cys | Leu | Ala | Gly | Arg | Ala | Leu | |
| 1 | | | | 5 | | | | | 10 | | | | | 15 | | |
| gcc | gat | att | gtg | atg | acc | cag | act | cca | ctc | tct | ctg | tcc | gtc | acc | cct | 96 |
| Ala | Asp | Ile | Val | Met | Thr | Gln | Thr | Pro | Leu | Ser | Leu | Ser | Val | Thr | Pro | |
| | | | 20 | | | | | 25 | | | | | 30 | | | |
| gga | cag | ccg | gcc | tcc | atc | tcc | tgc | aag | tca | agt | cag | agc | ctc | tta | gat | 144 |
| Gly | Gln | Pro | Ala | Ser | Ile | Ser | Cys | Lys | Ser | Ser | Gln | Ser | Leu | Leu | Asp | |
| | 35 | | | | | 40 | | | | | 45 | | | | | |
| ggt | gat | gga | aag | aca | tat | ttg | aat | tgg | ttg | ctg | cag | aag | cca | ggc | cag | 192 |
| Gly | Asp | Gly | Lys | Thr | Tyr | Leu | Asn | Trp | Leu | Leu | Gln | Lys | Pro | Gly | Gln | |
| 50 | | | | | 55 | | | | | 60 | | | | | | |
| tct | cca | cag | cgc | cta | atc | tat | ctg | gtg | tct | aaa | ctg | gac | tct | gga | gtg | 240 |
| Ser | Pro | Gln | Arg | Leu | Ile | Tyr | Leu | Val | Ser | Lys | Leu | Asp | Ser | Gly | Val | |
| 65 | | | | | 70 | | | | | 75 | | | | | 80 | |
| cca | gat | agg | ttc | agt | ggc | agc | ggg | tca | ggg | aca | gat | ttc | aca | ctg | aaa | 288 |
| Pro | Asp | Arg | Phe | Ser | Gly | Ser | Gly | Ser | Gly | Thr | Asp | Phe | Thr | Leu | Lys | |
| | | | | 85 | | | | | 90 | | | | | 95 | | |
| atc | agc | cgg | gtg | gag | gct | gag | gat | gtt | ggg | gtt | tat | tac | tgc | tgg | caa | 336 |
| Ile | Ser | Arg | Val | Glu | Ala | Glu | Asp | Val | Gly | Val | Tyr | Tyr | Cys | Trp | Gln | |
| | | | 100 | | | | | 105 | | | | | 110 | | | |
| ggt | aca | cat | ttt | cct | cgg | acg | ttc | ggt | cag | ggc | acc | aag | ctg | gaa | atc | 384 |
| Gly | Thr | His | Phe | Pro | Arg | Thr | Phe | Gly | Gln | Gly | Thr | Lys | Leu | Glu | Ile | |
| | | 115 | | | | | 120 | | | | | 125 | | | | |
| aaa | cgt | acg | gtg | gcg | gcg | cca | tct | gtc | ttc | atc | ttc | ccg | cca | tct | gat | 432 |
| Lys | Arg | Thr | Val | Ala | Ala | Pro | Ser | Val | Phe | Ile | Phe | Pro | Pro | Ser | Asp | |
| 130 | | | | | 135 | | | | | 140 | | | | | | |
| gag | cag | ttg | aaa | tct | gga | act | gcc | tct | gtt | gtg | tgc | ctg | ctg | aat | aac | 480 |
| Glu | Gln | Leu | Lys | Ser | Gly | Thr | Ala | Ser | Val | Val | Cys | Leu | Leu | Asn | Asn | |
| 145 | | | | | 150 | | | | | 155 | | | | | 160 | |
| ttc | tat | ccc | aga | gag | gcc | aaa | gta | cag | tgg | aag | gtg | gat | aac | gcc | ctc | 528 |
| Phe | Tyr | Pro | Arg | Glu | Ala | Lys | Val | Gln | Trp | Lys | Val | Asp | Asn | Ala | Leu | |
| | | | | 165 | | | | | 170 | | | | | 175 | | |
| caa | tcg | ggt | aac | tcc | cag | gag | agt | gtc | aca | gag | cag | gac | agc | aag | gac | 576 |
| Gln | Ser | Gly | Asn | Ser | Gln | Glu | Ser | Val | Thr | Glu | Gln | Asp | Ser | Lys | Asp | |
| | | | 180 | | | | | 185 | | | | | 190 | | | |
| agc | acc | tac | agc | ctc | agc | agc | acc | ctg | acg | ctg | agc | aaa | gca | gac | tac | 624 |
| Ser | Thr | Tyr | Ser | Leu | Ser | Ser | Thr | Leu | Thr | Leu | Ser | Lys | Ala | Asp | Tyr | |
| | | 195 | | | | | 200 | | | | | 205 | | | | |
| gag | aaa | cac | aaa | gtc | tac | gcc | tgc | gaa | gtc | acc | cat | cag | ggc | ctg | agc | 672 |
| Glu | Lys | His | Lys | Val | Tyr | Ala | Cys | Glu | Val | Thr | His | Gln | Gly | Leu | Ser | |
| 210 | | | | | 215 | | | | | 220 | | | | | | |

```
tcg ccc gtc aca aag agc ttc aac agg gga gag tgt tag        711
Ser Pro Val Thr Lys Ser Phe Asn Arg Gly Glu Cys *
225                 230                 235

<210> SEQ ID NO 13
<211> LENGTH: 236
<212> TYPE: PRT
<213> ORGANISM: Homo sapiens

<400> SEQUENCE: 13

Met Arg Ala Trp Ile Phe Phe Leu Leu Cys Leu Ala Gly Arg Ala Leu
1               5                   10                  15

Ala Asp Ile Val Met Thr Gln Thr Pro Leu Ser Leu Ser Val Thr Pro
            20                  25                  30

Gly Gln Pro Ala Ser Ile Ser Cys Lys Ser Gln Ser Leu Leu Asp
        35                  40                  45

Gly Asp Gly Lys Thr Tyr Leu Asn Trp Leu Leu Gln Lys Pro Gly Gln
    50                  55                  60

Ser Pro Gln Arg Leu Ile Tyr Leu Val Ser Lys Leu Asp Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Trp Gln
            100                 105                 110

Gly Thr His Phe Pro Arg Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 14
<211> LENGTH: 1800
<212> TYPE: DNA
<213> ORGANISM: Homo sapiens
<220> FEATURE:
<221> NAME/KEY: CDS
<222> LOCATION: (1)...(1800)

<400> SEQUENCE: 14 atg ggt tgg agc ctc atc ttg ctc ttc ctt gtc gct gtt gct acg cgt    48
Met Gly Trp Ser Leu Ile Leu Leu Phe Leu Val Ala Val Ala Thr Arg
1               5                   10                  15 gtc ctg tcc cag gta caa ctg cag cag cct ggg gct gag ctg gtg aag    96
Val Leu Ser Gln Val Gln Leu Gln Gln Pro Gly Ala Glu Leu Val Lys
            20                  25                  30 cct ggg gcc tca gtg aag atg tcc tgc aag gct tct ggc tac aca ttt   144
Pro Gly Ala Ser Val Lys Met Ser Cys Lys Ala Ser Gly Tyr Thr Phe
        35                  40                  45
```

```
acc agt tac aat atg cac tgg gta aaa cag aca cct ggt cgg ggc ctg     192
Thr Ser Tyr Asn Met His Trp Val Lys Gln Thr Pro Gly Arg Gly Leu
    50                  55                  60 gaa tgg att gga gct att tat ccc gga aat ggt gat act tcc tac aat     240
Glu Trp Ile Gly Ala Ile Tyr Pro Gly Asn Gly Asp Thr Ser Tyr Asn
65                  70                  75                  80 cag aag ttc aaa ggc aag gcc aca ttg act gca gac aaa tcc tcc agc     288
Gln Lys Phe Lys Gly Lys Ala Thr Leu Thr Ala Asp Lys Ser Ser Ser
                85                  90                  95 aca gcc tac atg cag ctc agc agc ctg aca tct gag gac tct gcg gtc     336
Thr Ala Tyr Met Gln Leu Ser Ser Leu Thr Ser Glu Asp Ser Ala Val
            100                 105                 110 tat tac tgt gca aga tcg act tac tac ggc ggt gac tgg tac ttc aat     384
Tyr Tyr Cys Ala Arg Ser Thr Tyr Tyr Gly Gly Asp Trp Tyr Phe Asn
        115                 120                 125 gtc tgg ggc gca ggg acc acg gtc acc gtc tct gca gcg agc acc aag     432
Val Trp Gly Ala Gly Thr Thr Val Thr Val Ser Ala Ala Ser Thr Lys
130                 135                 140 ggc cca tcg gtc ttc ccc ctg gca ccc tcc tcc aag agc acc tct ggg     480
Gly Pro Ser Val Phe Pro Leu Ala Pro Ser Ser Lys Ser Thr Ser Gly
145                 150                 155                 160 ggc aca gcg gcc ctg ggc tgc ctg gtc aag gac tac ttc ccc gaa ccg     528
Gly Thr Ala Ala Leu Gly Cys Leu Val Lys Asp Tyr Phe Pro Glu Pro
                165                 170                 175 gtg acg gtg tcg tgg aac tca ggc gcc ctg acc agc ggc gtg cac acc     576
Val Thr Val Ser Trp Asn Ser Gly Ala Leu Thr Ser Gly Val His Thr
            180                 185                 190 ttc ccg gct gtc cta cag tcc tca gga ctc tac tcc ctc agc agc gtg     624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac     672
Val Thr Val Pro Ser Ser Ser Leu Gly Thr Gln Thr Tyr Ile Cys Asn
210                 215                 220 gtg aat cac aag ccc agc aac acc aag gtg gac aag aaa gtt gag ccc     720
Val Asn His Lys Pro Ser Asn Thr Lys Val Asp Lys Lys Val Glu Pro
225                 230                 235                 240 aaa tct tgt gac aaa act cac aca tgc cca ccg tgc cca gca cct gaa     768
Lys Ser Cys Asp Lys Thr His Thr Cys Pro Pro Cys Pro Ala Pro Glu
                245                 250                 255 ctc ctg ggg gga ccg tca gtc ttc ctc ttc ccc cca aaa ccc aag gac     816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac     864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc     912
Val Ser His Glu Asp Pro Glu Val Lys Phe Asn Trp Tyr Val Asp Gly
    290                 295                 300 gtg gag gtg cat aat gcc aag aca aag ccg cgg gag gag cag tac aac     960
Val Glu Val His Asn Ala Lys Thr Lys Pro Arg Glu Glu Gln Tyr Asn
305                 310                 315                 320 agc acg tac cgt gtg gtc agc gtc ctc acc gtc ctg cac cag gac tgg    1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca    1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cga gaa    1104
Ala Pro Ile Glu Lys Thr Ile Ser Lys Ala Lys Gly Gln Pro Arg Glu
```

```
                       355                 360                 365
cca cag gtg tac acc ctg ccc cca tcc cgg gat gag ctg acc aag aac     1152
Pro Gln Val Tyr Thr Leu Pro Pro Ser Arg Asp Glu Leu Thr Lys Asn
            370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc     1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc     1392
Ser Val Met His Glu Ala Leu His Asn His Tyr Thr Gln Lys Ser Leu
    450                 455                 460 tcc ctg tct ccg ggt aaa ggt ggc ggt ggc tcg ggc ggt ggt ggg tcg     1440
Ser Leu Ser Pro Gly Lys Gly Gly Gly Gly Ser Gly Gly Gly Gly Ser
465                 470                 475                 480 gag gag gag ctg cag gtg att cag cct gac aag tcc gtg ttg gtt gca     1488
Glu Glu Glu Leu Gln Val Ile Gln Pro Asp Lys Ser Val Leu Val Ala
                485                 490                 495 gct gga gag aca gcc act ctg cgc tgc act gcg acc tct ctg atc cct     1536
Ala Gly Glu Thr Ala Thr Leu Arg Cys Thr Ala Thr Ser Leu Ile Pro
            500                 505                 510 gtg ggg ccc atc cag tgg ttc aga gga gct gga cca ggc cgg gaa tta     1584
Val Gly Pro Ile Gln Trp Phe Arg Gly Ala Gly Pro Gly Arg Glu Leu
        515                 520                 525 atc tac aat caa aaa gaa ggc cac ttc ccc cgg gta aca act gtt tca     1632
Ile Tyr Asn Gln Lys Glu Gly His Phe Pro Arg Val Thr Thr Val Ser
    530                 535                 540 gac ctc aca aag aga aac aac atg gac ttt tcc atc cgc atc ggt aac     1680
Asp Leu Thr Lys Arg Asn Asn Met Asp Phe Ser Ile Arg Ile Gly Asn
545                 550                 555                 560 atc acc cca gca gat gcc ggc acc tac tac tgt gtg aag ttc cgg aaa     1728
Ile Thr Pro Ala Asp Ala Gly Thr Tyr Tyr Cys Val Lys Phe Arg Lys
                565                 570                 575 ggg agc ccc gat gac gtg gag ttt aag tct gga gca ggc act gag ctg     1776
Gly Ser Pro Asp Asp Val Glu Phe Lys Ser Gly Ala Gly Thr Glu Leu
            580                 585                 590 tct gtg cgc gcc aaa ccc tct tga                                     1800
Ser Val Arg Ala Lys Pro Ser *
        595

<210> SEQ ID NO 15
<211> LENGTH: 599
<212> TYPE: PRT
<213> ORGANISM: Homo sapiens

<400> SEQUENCE: 15

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45
```

-continued

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys Gly Gly Gly Gly Ser Gly Gly Gly Gly Ser

-continued

```
            465                 470                 475                 480

Glu Glu Glu Leu Gln Val Ile Gln Pro Asp Lys Ser Val Leu Val Ala
                        485                 490                 495

Ala Gly Glu Thr Ala Thr Leu Arg Cys Thr Ala Thr Ser Leu Ile Pro
                        500                 505                 510

Val Gly Pro Ile Gln Trp Phe Arg Gly Ala Gly Pro Gly Arg Glu Leu
                        515                 520                 525

Ile Tyr Asn Gln Lys Glu Gly His Phe Pro Arg Val Thr Thr Val Ser
                        530                 535                 540

Asp Leu Thr Lys Arg Asn Asn Met Asp Phe Ser Ile Arg Ile Gly Asn
        545                 550                 555                 560

Ile Thr Pro Ala Asp Ala Gly Thr Tyr Tyr Cys Val Lys Phe Arg Lys
                        565                 570                 575

Gly Ser Pro Asp Asp Val Glu Phe Lys Ser Gly Ala Gly Thr Glu Leu
                        580                 585                 590

Ser Val Arg Ala Lys Pro Ser
                        595
```

SIRP ALPHA-ANTIBODY FUSION PROTEINS

CROSS REFERENCE

This application claims benefit and is a Divisional of application Ser. No. 15/502,475 filed Feb. 7, 2017, which is a 371 application and claims the benefit of PCT Application No. PCT/US2015/044304, filed Aug. 7, 2015, which claims benefit of U.S. Provisional Patent Application No. 62/035,273, filed Aug. 8, 2014, which applications are incorporated herein by reference in their entirety.

BACKGROUND OF THE INVENTION

Macrophages clear pathogens and damaged or aged cells from the blood stream via phagocytosis. Cell-surface CD47 interacts with its receptor on macrophages, SIRPα, to inhibit phagocytosis of normal, healthy cells. CD47 is a broadly expressed transmembrane glycoprotein with a single Ig-like domain and five membrane spanning regions, which functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including hematopoietic stem cells.

SIRPα inhibits the phagocytosis of host cells by macrophages, where the ligation of SIRPα on macrophages by CD47 expressed on the host target cell generates an inhibitory signal mediated by SHP-1 that negatively regulates phagocytosis. SIRPα acts to detect signals provided by "self," to negatively control innate immune effector function against these cells.

In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

The present invention provides immunoglobulin fusion proteins that inhibit the interaction of CD47 with SIRP leading to phagocytosis as a result of disrupting the negative regulatory signal.

SUMMARY OF THE INVENTION

Compositions and methods are provided relating to fusion proteins, herein termed SIRPabodies, that comprise an immunoglobulin variable region, which may specifically bind a tumor antigen, viral antigen, etc., fused to a sequence comprising a binding domain of SIRPα. The binding domain of SIRPα comprises at least the N-terminal Ig-like domain of SIRPα, and may further comprise additional SIRPα sequences. The SIRPabodies find use in therapeutic methods that benefit from the combined activity of blocking CD47 activity, and antibody targeting, e.g. in the treatment of cancer, etc. In some specific embodiments, the SIRPabody comprises an anti-CD20 binding domain and a SIRPα binding domain. In other specific embodiments the SIRPabody comprises an anti-CD99 binding domain and a SIRPα binding domain. In other specific embodiments the SIRPabody comprises an anti-TIM3 binding domain and a SIRPα binding domain.

SIRPabody polypeptide molecules of the invention comprise two functional domains: an immunoglobulin variable region domain, and the N-terminal Ig-like domain of SIRPα, for example as shown in SEQ ID NO:1 and variants thereof, including without limitation allelic polymorphisms. In some embodiments the SIRPabody comprises a first and a second polypeptide chain, which first polypeptide chain comprises (i) a first domain comprising a binding region of a light chain variable domain of an immunoglobulin ($V_L$) specific for a first epitope; and a second polypeptide comprising (i) a first domain comprising a binding region of a heavy chain variable region domain of an immunoglobulin ($V_H$) specific for a first epitope; and (ii) a second domain comprising the N-terminal Ig-like domain of SIRPα. In some embodiments, the first polypeptide and the second polypeptide further comprise the respective heavy and light chain constant region domains of the immunoglobulin, i.e. $C_L$ and $C_H$. In some embodiments, the second polypeptide comprises the N-terminal Ig-like domain of SIRPα fused to the amino terminus of the $V_H$ domain (N-terminal SIRPabody, or NH-SIRPabody). In other embodiments the second polypeptide comprises the N-terminal Ig-like domain of SIRPα fused to the amino terminus of the $C_H$ domains (C-terminal SIRPabody, or CH-SIRPabody).

In an alternative embodiment, the SIRPabody comprises a first and a second polypeptide chain, which first polypeptide chain comprises (i) a first domain comprising a binding region of a light chain variable domain of an immunoglobulin ($V_L$) specific for a first epitope; and (ii) a second domain comprising the N-terminal Ig-like domain of SIRPα; and a second polypeptide comprising (i) a first domain comprising a binding region of a heavy chain variable region domain of an immunoglobulin ($V_H$) specific for a first epitope. In some embodiments, the first polypeptide and the second polypeptide further comprise the respective heavy and light chain constant region domains of the immunoglobulin, i.e. $C_L$ and $C_H$. In some embodiments, the first polypeptide comprises the N-terminal Ig-like domain of SIRPα fused to the amino terminus of the $V_L$ domain (NL-SIRPabody). In other embodiments the second polypeptide comprises the N-terminal Ig-like domain of SIRPα fused to the amino terminus of the $C_L$ domains (CL-SIRPabody).

The SIRPα domain and the $V_H$ or $C_H$ domains may be separated by a short linker. The peptide linker may be 0, 1, 2, 3, 4, 5, 6, 7, 8, 9, 10, 11, 12, 13, 14, 15, 16, 17, 18, 19, 20 amino acids in length, and is of sufficient length and amino acid composition to minimize steric hindrance between the binding domains. In some embodiments the linker is glycine and/or serine; exemplary is one or more subunits of SEQ ID NO:2. Alternatively the sequence of the constant region can provide the linker, for example as shown in SEQ ID NO:3.

The SIRPabodies of the invention are particularly efficacious in the treatment of disease, e.g. increasing phagocytosis of living CD47 expressing cells. Treatment may be systemic or localized, e.g. delivery by intratumoral injection, etc. In certain embodiments, methods are provided for a targeted cytotoxicity therapy that (a) blocks CD47 activity through the SIRPα binding domain and may additionally (b) provide antibody mediated targeting and/or cell killing as a result of binding to the immunoglobulin variable region domain. A targeted cell population suspected of expressing on the cell surface the cognate antigen for the immunoglobulin variable region domain of a SIRPabody is contacted with an effective dose of the SIRPabody, where the dose is sufficient to increase killing of the targeted cells, relative to the level of killing obtained with the immunoglobulin alone. In such embodiments, the $F_c$ region of the immunoglobulin is generally present, and the activity may be compared to the activity of the intact immunoglobulin.

In some such embodiments the cognate antigen is CD20. Antibodies that specifically target CD20 are well known in the art, including human and humanized antibodies available for therapeutic purposes, e.g. Tositumumab, Rituximab, Ibritumomab Tiuxetan, Veltuzumab, AME-133v, Ofatumumab, R7159, etc. The targeted cells in such an embodiment are CD20 positive cancer cells. The contacting may be performed in vivo, and includes the treatment of malignancies, including without limitation B cell non-Hodgkin lymphomas, hairy cell leukemia, B-cell chronic lymphocytic leukemia, melanoma cancer stem cells, etc. In some embodiments, treatment of an individual with such a malignancy comprises the steps of administering an effective dose of a SIRPabody that causes increased killing of CD20+ malignant cells, i.e. to increase by greater than about 20%, to increase by greater than about 30%, to increase by greater than about 40%, to increase by greater than about 50%, to increase by greater than about 75%, to increase by greater than about 90%, to increase by greater than about 95%, to increase by greater than about 99% or more relative to treatment with the corresponding immunoglobulin lacking the SIRPα binding domain. A synergistic response may be obtained, where, for example, the reduction in tumor cell population with the SIRPabody is greater than the reduction obtained with one or both of soluble SIRPα binding domain and anti-CD20 immunoglobulin. SIRPabodies for this purpose include without limitation CD20-2GL-SIRPα, CD20-4GL-SIRPα, and SIRPα-CD20 provided herein.

In other embodiments the cognate antigen is CD99. Antibodies specific for CD99 and are known in the art and commercially available, e.g. 12E7, HCD99, F21, O13, etc. CD99 is expressed on a number of cancers, including without limitation Ewing's sarcoma tumors, thymic tumors, synovial sarcoma, haemangiopericytoma, and meningioma, small cell lung cancer, AML, diffuse large B-cell lymphoma (DLBCL), etc. In some embodiments, treatment of an individual with such a malignancy comprises the steps of administering an effective dose of a SIRPabody that causes increased killing of CD99+ malignant cells, i.e. to increase by greater than about 20%, to increase by greater than about 30%, to increase by greater than about 40%, to increase by greater than about 50%, to increase by greater than about 75%, to increase by greater than about 90%, to increase by greater than about 95%, to increase by greater than about 99% or more relative to treatment with the corresponding immunoglobulin lacking the SIRPα binding domain. A synergistic response may be obtained, where, for example, the reduction in tumor cell population with the SIRPabody is greater than the reduction obtained with one or both of soluble SIRPα binding domain and anti-CD99 immunoglobulin.

In other embodiments the cognate antigen is TIM3. Antibodies specific for TIM3 and are known in the art and commercially available, e.g. 1F38-2E2, etc. CD99 is expressed on certain cancer cells, including without limitation AML. In some embodiments, treatment of an individual with such a malignancy comprises the steps of administering an effective dose of a SIRPabody that causes increased killing of TIM3+ malignant cells, i.e. to increase by greater than about 20%, to increase by greater than about 30%, to increase by greater than about 40%, to increase by greater than about 50%, to increase by greater than about 75%, to increase by greater than about 90%, to increase by greater than about 95%, to increase by greater than about 99% or more relative to treatment with the corresponding immunoglobulin lacking the SIRPα binding domain. A synergistic response may be obtained, where, for example, the reduction in tumor cell population with the SIRPabody is greater than the reduction obtained with one or both of soluble SIRPα binding domain and anti-TIM3 immunoglobulin.

In other related embodiments, an anti-CD20 SIRPabody is used in a method of treating autoimmune diseases with a B cell component, including without limitation rheumatoid arthritis, multiple sclerosis, Type I diabetes, Type II diabetes, systemic lupus erythematosus, and the like. In such methods targeted cytotoxicity (a) blocks CD47 activity through the SIRPα binding domain and (b) provides antibody mediated cell killing through the immunoglobulin variable region domain. A targeted B cell population expressing CD20 is contacted with an effective dose of the SIRPabody, where the dose is sufficient to increase killing of the targeted cells, relative to the level of killing obtained with the immunoglobulin alone. In such embodiments, the $F_c$ region of the immunoglobulin is generally present, and the activity may be compared to the activity of the intact immunoglobulin.

In yet another embodiment of the present invention, the SIRPabodies of the invention can be used to treat a variety of diseases and disorders. Accordingly, the present invention is directed to a method for treating a disease or disorder comprising administering to a patient in need thereof an effective amount of a SIRPabody of the invention, in which the SIRPabody has been selected to provide a specific level of targeting correlated with the binding specificity of the immunoglobulin, coupled with blocking CD47 activity. Such methods include those contemplated by U.S. Pat. No. 8,562,997, international applications US2014/014905 and US2014/035167, each herein specifically incorporated by reference. In further such embodiments of the invention, the antigen is a tumor antigen.

The immunoglobulin portion of the SIRPabody may comprise constant region sequences that are characteristic of mouse, rabbit, primate, human, etc., antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an immunoglobulin portion of the SIRPabody utilized in accordance with the present invention is in a format selected from, but not limited to, IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular Immuno Pharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®.

For example, the SIRPabody may comprise a full length chimeric or humanized antibody, e.g. having a human immunoglobulin constant region of any isotype, e.g. IgG1, IgG2a, IgG2b, IgG3, IgG4, IgA, etc. or an antibody fragment, e.g. a F(ab')$_2$ fragment, and F(ab) fragment, etc. Furthermore, the SIRPabody may be labeled with a detectable label, immobilized on a solid phase and/or conjugated with a heterologous compound.

The invention further provides: isolated nucleic acid encoding the SIRPabodies and variants thereof; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising one or more SIRPabodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 8: SIRPα-rituximab bispecific reagents have reduced affinity to CD47 relative to anti-CD47. Kinetic association and dissociation parameters, along with calculated affinity (Kd) were measured by surface plasmon resonance using Biacore. The surface was coated with the indicated antibodies via amine-coupling prior to exposure to CD47-His analyte.

(FIG. 11A) Schematic of the experimental design to assay for selectivity in binding to dual antigen-expressing cells in the presence of an excess of CD47-only expressing cells. GFP labeled CD20+CD47+ cells were mixed with a 10-fold excess of CD20−CD47+ human red blood cells (RBCs). Cell mixtures were incubated with primary antibody prior to staining with PE anti-human Fcγ secondary and 10 μg/ml APC anti-CD47, and analyzed by flow cytometry. (FIG. 11B, FIG. 11C) Tumor cells were distinguished from RBCs on the basis of GFP expression. The indicated primary antibodies were used at 10 ug/ml and binding to cells was detected with secondary antibody staining (PE anti-human Fc). 2B8=anti-CD20, B6H12=anti-CD47. (FIG. 11D) Binding of APC anti-CD47 to cells is reported as MFI normalized to isotype control.

(FIG. 13A) NSG mice transplanted subcutaneously with luciferase-expressing Raji cells were treated with daily injections of 200 μg mouse IgG control, anti-CD47, SIRPα-Fc, rituximab, CD20-2GL-SIRPα, or 200 μg anti-CD47+ 200 μg rituximab. (n=5 per treatment group). Luciferase imaging was averaged for all mice in each treatment group. Arrows indicate start (day 7) and stop (day 20) of treatment. Rituximab treatment was compared to CD20-2GL-SIRPα at day 42 (*p<0.05 by t test). (FIG. 13B) Kaplan-Meier survival analysis with p-values calculated comparing rituximab single antibody treatment to combination treatment/CD20-2GL-SIRPα. (*p<0.05 by log-rank Mantel-Cox test).

(FIG. 14A) NSG mice were transplanted subcutaneously with Raji-luciferase cells. Seven days later, mice were treated with 14 daily doses of 200 µg IgG (n=15), SIRPα-Fc (n=15), rituximab (n=15), CD20-2GL-SIRPα HC (n=15) or 200 µg SIRPα-Fc+200 µg rituximab (n=10). Expansion of Raji-luciferase cells was evaluated by bioluminescence imaging. Each point represents a measurement from an independent mouse and lines indicate median values for each treatment group. p values were derived by t test and compare rituximab to CD20-2GL-SIRPα HC for each time point. (FIG. 14B) Kaplan-Meier survival analysis was performed. Arrows indicated start (day 7) and stop (day 21) of treatment. Statistical analysis was performed by Mantel-Cox and compares rituximab to CD20-2GL-SIRPα HC. (FIG. 14C) NSG mice were transplanted intravenously with Raji-luciferase cells. Four days later, mice were administered 21 daily doses of antibody treatment as described in (FIG. 14A). Each point represents a measurement from an independent mouse (n=10). Lines indicate mean values for each treatment group. p values were derived by t test and compare rituximab to CD20-2GL-SIRPα HC for each time point. (FIG. 14D) Kaplan-Meier survival analysis was performed. Arrows indicated start (day 4) and stop (day 25) of treatment. Statistical analysis was performed by Mantel-Cox and compares rituximab to CD20-2GL-SIRPα HC.

DETAILED DESCRIPTION OF THE INVENTION

Figure 1A:
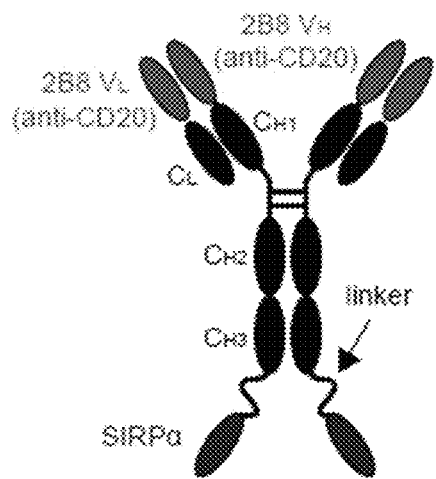
FIG. 1A-1B: Schematic of SIRPα-rituximab reagents (SIRPabodies). The N-terminal immunoglobulin fold from wild type SIRPα (green) was engineered onto either the N or C terminus of the heavy chain of rituximab (clone 2B8). The light chain sequence is provided as SEQ ID NO:4, where the signal sequence is amino acid residues 1-22. A polyglycine serine linker SEQ ID NO:2, $(GGGGS)_2$ or $(GGGGS)_4$ was used to fuse SIRPα onto the C terminus of the heavy chain to create CD20-2GL-SIRPα (SEQ ID NO:6) or CD20-4GL-SIRPα (SEQ ID NO:10), respectively. The signal sequence is amino acid residues 1-19, the linker is residues 471-480 or 471-490, respectively. The SIRPα sequence is residues 481-599, or 490-609, respectively. A linker derived from the N terminal amino acids of the CH1 domain SEQ ID NO:3, (ASTKGPSVFPLAP) was used to fuse SIRPα onto the N terminus of the heavy chain, shoan as SEQ ID NO:8, where the signal sequence is amino acid residues 1-17, the SIRPα sequence is residues 18-136, the linker is residues 137-149.

SIRPabodies comprise an immunoglobulin variable region, which may specifically bind a tumor antigen, viral antigen, etc., fused to a sequence comprising a binding domain of SIRPα. The binding domain of SIRPα comprises at least the N-terminal Ig-like domain of SIRPα, and may further comprise additional SIRPα sequences. The SIRPabodies find use in therapeutic methods that benefit from the combined activity of blocking CD47 activity, and antibody targeting, e.g. in the treatment of cancer, etc. In some specific embodiments, the SIRPabody comprises anti-CD20 activity and a SIRPα binding domain.

Definitions

In the description that follows, a number of terms conventionally used in the field of cell culture are utilized. In order to provide a clear and consistent understanding of the specification and claims, and the scope to be given to such terms, the following definitions are provided.

The terms "CD47 binding domain agents", with respect to the interaction between SIRPα and its ligand CD47 refer to molecules that prevent the binding of SIRPα and CD47. For development purposes the binding may be performed under experimental conditions, e.g. using isolated proteins as binding partners, using portions of proteins as binding partners, using yeast display of proteins or portions of proteins as binding partners, and the like.

For therapeutic purposes the binding of SIRPα and CD47 is typically an event between two cells, where each cell expresses one of the binding partners. Of particular interest is the expression of SIRPα on phagocytic cells, such as macrophages; and the expression of CD47 on cells that may be targets for phagocytosis, e.g. tumor cells, circulating hematopoietic cells, and the like. Inhibitors may be identified using in vitro and in vivo assays for receptor or ligand binding or signaling.

For the purposes of the invention a blocking agent comprises a SIRPα binding domain, for example the N-terminal immunoglobulin fold domain of SEQ ID NO:1, and variants, including without limitation allelic variants. Relative to the human native SIRPα sequences, (for example see Genbank accession no. AAH75849, and variants NM_080792.2; XM_005260670.1; XM_005260669.1; NM_001040023.1; NM_001040022.1, herein specifically incorporated by reference) a soluble SIRPα binding domain may comprise the d1 domain of SIRPα, corresponding to residues 31 to 149 of the native full-length human protein. In such embodiments, the soluble SIRPα binding domain may consist of all or a portion of the d1 domain; may further comprise one or more amino acids from SIRPα outside of the d1 domain.

SIRPα binding domains may be at least about 100 amino acids in length, at least about 110, at least about 120, at least about 150, at least about 200 amino acids in length, up to the full-length of the wild-type protein at the transmembrane domain, i.e. about 343 amino acids in length, and is optionally fused to a heterologous polypeptide.

A low affinity SIRPα sequence is generally preferred for the purposes of the invention, i.e. an affinity equivalent to the affinity of the native protein for binding with CD47. However, in some embodiments an increased affinity may be preferred, for which purpose the variants set forth in, for example, WO 2013/109752 (herein specifically incorporated by reference) may be used.

The SIRPα sequence may be a variant of the native human sequence. As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. A polypeptide may have a characteristic sequence element comprised of a plurality of amino acids having designated positions relative to one another in linear or three-dimensional space and/or contributing to a particular biological function. For example, a variant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc. Also included are mammals such as domestic and other species of canines, felines, and the like.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

Non-Hodgkin lymphomas (NHL) are a heterogeneous group of disorders involving malignant monoclonal proliferation of lymphoid cells in lymphoreticular sites, including lymph nodes, bone marrow, the spleen, the liver, and the gastrointestinal tract. Presenting symptoms usually include peripheral lymphadenopathy. Compared with Hodgkin lymphoma, there is a greater likelihood of disseminated disease at the time of diagnosis. However, NHL is not one disease but rather a category of lymphocyte malignancies. These types can be divided into aggressive (fast-growing) and indolent (slow-growing) types, and they can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, precursor B-lymphoblastic lymphoma, and mantle cell lymphoma, among others. T-cell non-Hodgkin lymphomas include mycosis fungoides, anaplastic large cell lymphoma, and precursor T-lymphoblastic lymphoma. Lymphomas that occur after bone marrow or stem cell transplantation are usually B-cell non-Hodgkin lymphomas. Prognosis and treatment depend on the stage and type of disease.

Diffuse large B-cell lymphoma (DLBCL) is the most common subtype of non-Hodgkin lymphoma (NHL), accounting for approximately 30% of all newly diagnosed cases and more than 80% of aggressive lymphomas. Recent insights into the pathogenesis of DLBCL suggest that it is a heterogeneous group of B-cell lymphomas rather than a single clinicopathologic entity. Multiple histologic subtypes and morphologic variants are recognized, a variety of molecular and genetic abnormalities are variably present, and patients exhibit a wide range of clinical presentations and outcomes. Gene-expression profiling studies have identified at least 3 distinct molecular subtypes of DLBCL, one with an expression profile similar to normal germinal center B cells (GCB subtype), one mimicking activated peripheral-blood B cells (ABC subtype), and a third, primary mediastinal large B-cell lymphoma (PMBCL), typically presenting with mediastinal lymphadenopathy and displaying some molecular genetic similarities to Hodgkin lymphoma. A small number of cases do not fit into any of these categories and have been designated as "unclassifiable."

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with ocular disease. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

In some embodiments, treatment is accomplished by administering a SIRPabody in combination with a cytotoxic agent. One exemplary class of cytotoxic agents are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

"Concomitant administration" of a known cancer therapeutic drug with a pharmaceutical composition of the present invention means administration of the drug and SIRPabody at such time that both the known drug and the composition of the present invention will have a therapeutic effect. Such concomitant administration may involve concurrent (i.e. at the same time), prior, or subsequent administration of the drug with respect to the administration of a compound of the invention. A person of ordinary skill in the art would have no difficulty determining the appropriate timing, sequence and dosages of administration for particular drugs and compositions of the present invention.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain.

Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity.

As is known in the art, affinity and/or other binding attributes of Fc regions for Fc receptors can be modulated through glycosylation or other modification. In some embodiments, SIRPabodies produced and/or utilized in accordance with the present invention may include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology.

In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular Immuno Pharmaceuticals ("SMIPs™"), single chain or Tandem diabodies (TendAbe), VHHs, Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®.

As used herein, the term "antibody-dependent cellular cytotoxicity" or "ADCC" refers to a phenomenon in which target cells bound by antibody are killed by immune effector cells. Without wishing to be bound by any particular theory, ADCC is typically understood to involve Fc receptor (FcR)-bearing effector cells can recognizing and subsequently killing antibody-coated target cells (e.g., cells that express on their surface specific antigens to which an antibody is bound). Effector cells that mediate ADCC can include immune cells, including but not limited to one or more of natural killer (NK) cells, macrophage, neutrophils, eosinophils.

The term "antigen", as used herein, refers to an agent that elicits an immune response; and/or for the purposes of the invention, (ii) an agent that binds to an antibody. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source).

The term "anti-CD20 antibody" refers herein to monoclonal or polyclonal antibodies with specificity for the polypeptide CD20. Antibodies with specificity for CD20 can be prepared by methods that are well understood in the art. Preferred antibody compositions are ones that have been selected for antibodies directed against a polypeptide or polypeptides of CD20. Particularly preferred polyclonal antibody preparations are ones that contain only antibodies directed against a polypeptide or polypeptides of CD20. Anti-CD20 antibodies that are suitable for use in the current invention would include, for example, rituximab, ibritumomab tiuxetan, tositumomab, AME-133v (Applied Molecular Evolution), Ocrelizumab (Roche), Ofatumumab (Genmab), TRU-015 (Trubion) and IMMU-106 (Immunomedics). In one embodiment, the anti-CD20 antibody is rituximab.

"CD20", "CD20 protein", and "CD20 polypeptide" are used interchangeably herein to refer to a polypeptide encoded by a member of the membrane-spanning 4A gene family. This gene, referred to as "MS4A1", "Membrane-spanning 4-domains, subfamily A, member 1", "B1" and "B-lymphocyte surface antigen B1", encodes a non-glycosylated phosphoprotein of 297 amino acids, as described at, for example, Genbank NM_152866 and Genbank NM_021950 (alternative splice variants that encode the same protein). CD20 polypeptide is expressed on the surface of B cells beginning at the late pre-B cell phase of development, and plays a role in B cell proliferation.

Antibodies targeting tumor antigens have been approved for use in treating cancers, and are rapidly becoming standard of care. A non-comprehensive list of certain human antigens targeted by known, available antibody agents, and notes certain cancer indications for which the antibody agents have been proposed to be useful:

| | | |
|---|---|---|
| CD2 | Siplizumab | Non-Hodgkin's Lymphoma |
| CD3 | UCHT1 | Peripheral or Cutaneous T-cell |
| CD4 | HuMax-CD4 | Lymphoma |
| CD19 | SAR3419, MEDI-551 | Diffuse Large B-cell Lymphoma |
| CD19 and CD3 or CD22 | Bispecific antibodies such as Blinatumomab, DT2219ARL | Non-Hodgkin's Lymphoma |
| CD20 | Rituximab, Veltuzumab, Tositumomab, Ofatumumab, Ibritumomab, Obinutuzumab, | B cell malignancies (Non-Hodgkin's lymphoma, Chronic lymphocytic leukemia) |
| CD22 (SIGLEC2) | Inotuzumab, tetraxetan, CAT-8015, DCDT2980S, Bectumomab | Chemotherapy-resistant hairy cell leukemia, Hodgkin's lymphoma |
| CD30 | Brentuximab vedotin | |
| CD33 | Gemtuzumab ozogamicin (Mylotarg) | Acute myeloid leukemia |
| CD37 | TRU-016 | Chronic lymphocytic leukemia |
| CD38 | Daratumumab | Multiple myeloma, hematological tumors |
| CD40 | Lucatumumab | Non-Hodgkin's lymphoma |
| CD52 | Alemtuzumab (Campath) | Chronic lymphocytic leukemia |
| CD56 (NCAM1) | Lorvotuzumab | Small Cell Lung Cancer |
| CD66e (CEA) | Labetuzumab | Breast, colon and lung tumors |

-continued

| | | |
|---|---|---|
| CD70 | SGN-75 | Non-Hodgkin's lymphoma |
| CD74 | Milatuzumab | Non-Hodgkin's lymphoma |
| CD138 (SYND1) | BT062 | Multiple Myeloma |
| CD152 (CTLA-4) | Ipilimumab | Metastatic melanoma |
| CD221 (IGF1R) | AVE1642, IMC-A12, MK-0646, R150, CP 751871 | Glioma, lung, breast, head and neck, prostate and thyroid cancer |
| CD254 (RANKL) | Denosumab | Breast and prostate carcinoma |
| CD261 (TRAILR1) | Mapatumumab | Colon, lung and pancreas tumors and haematological malignancies |
| CD262 (TRAILR2) | HGS-ETR2, CS-1008 | |
| CD326 (Epcam) | Edrecolomab, 17-1A, IGN101, Catumaxomab, Adecatumumab | Colon and rectal cancer, malignant ascites, epithelial tumors (breast, colon, lung) |
| CD309 (VEGFR2) | IM-2C6, CDP791 | Epithelium-derived solid tumors |
| CD319 (SLAMF7) | HuLuc63 | Multiple myeloma |
| CD340 (HER2) | Trastuzumab, Pertuzumab, Ado-trastuzumab emtansine | Breast cancer |
| CAIX (CA9) | cG250 | Renal cell carcinoma |
| EGFR (c-erbB) | Cetuximab, Panitumumab, nimotuzumab and 806 | Solid tumors including glioma, lung, breast, colon, and head and neck tumors |
| EPHA3 (HEK) | KB004, IIIA4 | Lung, kidney and colon tumors, melanoma, glioma and haematological malignancies |
| Episialin | Epitumomab | Epithelial ovarian tumors |
| FAP | Sibrotuzumab and F19 | Colon, breast, lung, pancreas, and head and neck tumors |
| HLA-DR beta | Apolizumab | Chronic lymphocytic leukemia, non-Hodkin's lymphoma |
| FOLR-1 | Farletuzumab | Ovarian tumors |
| 5T4 | Anatumomab | Non-small cell lung cancer |
| GD3/GD2 | 3F8, ch14.18, KW-2871 | Neuroectodermal and epithelial tumors |
| gpA33 | huA33 | Colorectal carcinoma |
| GPNMB | Glembatumumab | Breast cancer |
| HER3 (ERBB3) | MM-121 | Breast, colon, lung, ovarian, and prostate tumors |
| Integrin αVβ3 | Etaracizumab | Tumor vasculature |
| Integrin α5β1 | Volociximab | Tumor vasculature |
| Lewis-Y antigen | hu3S193, IgN311 | Breast, colon, lung and prostate tumors |
| MET (HGFR) | AMG 102, METMAB, SCH900105 | Breast, ovary and lung tumors |
| Mucin-1/CanAg | Pemtumomab, oregovomab, Cantuzumab | Breast, colon, lung and ovarian tumors |
| PSMA | ADC, J591 | Prostate Cancer |
| Phosphatidylserine | Bavituximab | Solid tumors |
| TAG-72 | Minretumomab | Breast, colon and lung tumors |
| Tenascin | 81C6 | Glioma, breast and prostate tumours |
| VEGF | Bevacizumab | Tumour vasculature |

As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment.

For example, in some embodiments, the term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy, such as a B cell lymphoma, or helps achieve or prolong remission of a malignancy.

A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof.

In addition, regression of a particular tumor in an individual (e.g., as the result of treatments described herein) may also be assessed by taking samples of cancer cells from the site of a tumor such as a B cell lymphoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers, an increase in anti-angiogenic markers, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Methods of Use

The present invention provides methods for treating, reducing or preventing cancer, including without limitation hematopoietic cancers, and metastasis of cancers, by inhibiting the interaction between SIRPα and CD47 in a targeted manner, thereby increasing phagocytosis of tumor cells. Such methods include administering to a subject in need of treatment a therapeutically effective amount or an effective dose of a SIRPabody, where there immunoglobulin variable region of the SIRPabody specifically binds a cell surface protein on the tumor cell, particularly binding to CD20. Effective doses of the therapeutic entity of the present invention, e.g. for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated. Treatment dosages need to be titrated to optimize safety and efficacy.

In some embodiments, the dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including lymphomas, leukemias, carcinomas, melanomas, glioblastomas, sarcomas, myelomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

In one aspect, the invention provides SIRPabody polypeptides, and isolated nucleic acids encoding SIRPabody polypeptides. For recombinant production of the SIRPabody, the nucleic acid encoding it is inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The SIRPabody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Therapeutic formulations comprising one or more SIR-Pabodies of the invention are prepared for storage by mixing the SIRPabody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD47 associated disease.

The therapeutic dose may be at least about 0.01 μg/kg body weight, at least about 0.05 μg/kg body weight; at least about 0.1 μg/kg body weight, at least about 0.5 μg/kg body weight, at least about 1 μg/kg body weight, at least about 2.5 μg/kg body weight, at least about 5 μg/kg body weight, and not more than about 100 μg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the SIRPabody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Also within the scope of the invention are kits comprising the compositions (e.g., SIRPabodies and formulations thereof) of the invention and instructions for use. The kit can further contain a least one additional reagent, e.g. a chemotherapeutic drug, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Figure 1B:
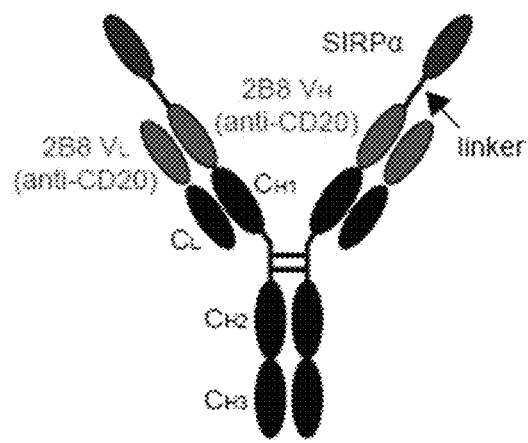

SIRPabodies were created with the aim of co-targeting CD47 and a second antigen. CD20 was chosen for this purpose. The N-terminal immunoglobulin fold from wild type human SIRPα was engineered onto either the N or C terminus of the heavy chain of rituximab, an established anti-CD20 antibody (FIG. 1A, 1B).

Figure 2:
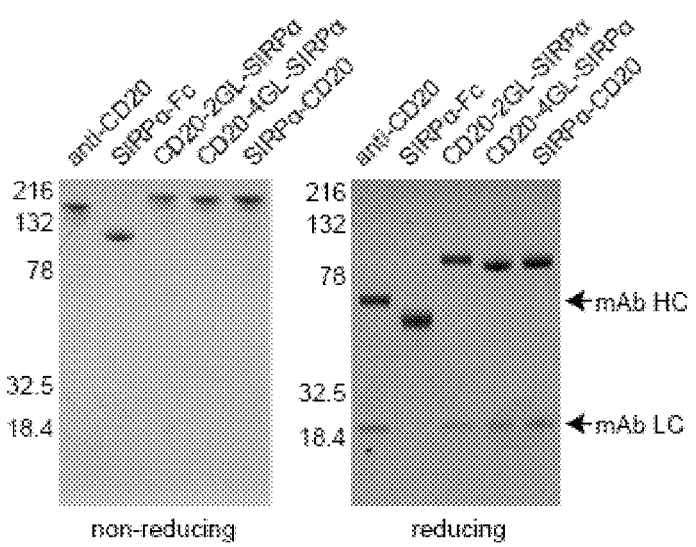
FIG. 2: Construction of SIRPα-rituximab bispecific reagents. SDS-PAGE analysis of the indicated purified antibodies under non-reducing (left) and reducing (right) conditions. Anti-CD20 antibody was included as a reference for the sizes of the parental heavy and light chains.

Production of recombinant SIRPα-rituximab bispecific reagents was confirmed by analysis of purified protein on reducing and non-reducing SDS-PAGE (FIG. 2).

Figure 3A:
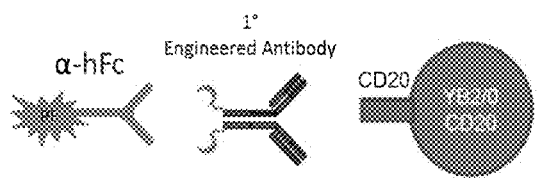
FIG. 3A-3B: SIRPα-rituximab bispecific reagents bind to CD20 on the cell surface. The indicated antibodies were used to stain rat YB2/0 cells engineered to express human CD20, but not human CD47 (CD20+CD47−) prior to detection with anti-human secondary antibody by flow cytometry. 2B8=anti-CD20, B6H12=anti-CD47.
Figure 3B:
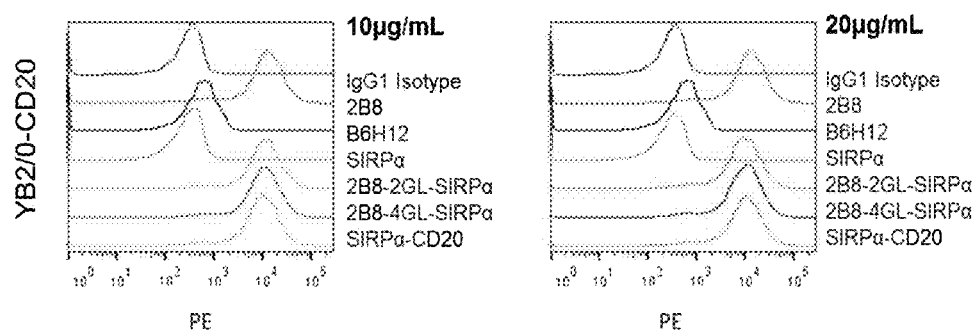
Figure 4:
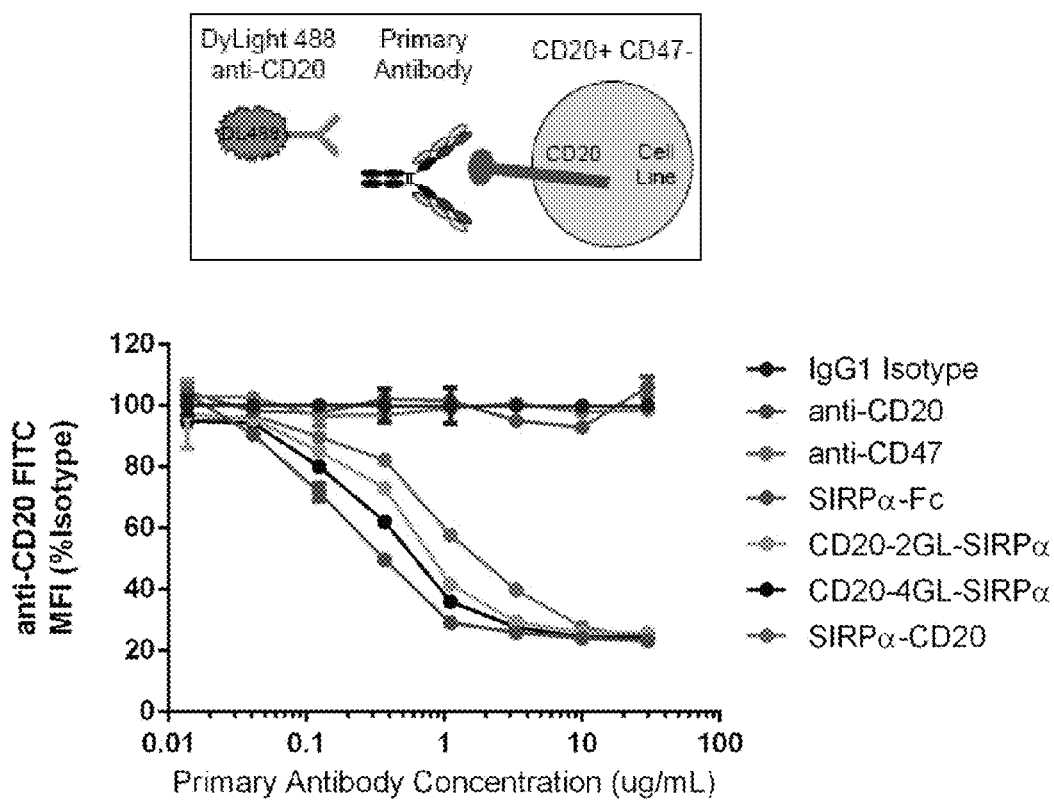
FIG. 4: SIRPα-rituximab bispecific reagents bind to CD20 with similar affinity as parental antibody. CD20+ CD47− YB2/0 cells were incubated with the indicated primary antibodies over a range of concentrations prior to staining with 10 μg/ml DyLight 488anti-CD20 and detection by flow cytometry. Mean fluorescence intensity (MFI) of the DyLight 488 signal for each condition was measured by flow cytometry.

Each SIRPabody (engineered bispecific variant) retained the ability to bind the CD20 antigen expressed on the cell surface (FIG. 3). Accordingly, when CD20-expressing cells were stained with SIRPabodies prior to incubation with DyLight 488anti-CD20, all antibodies masked the CD20 epitope preventing subsequent binding with DyLight 488anti-CD20 (FIG. 4).

Figure 5A:
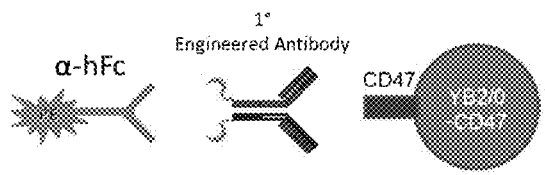
FIG. 5A-5B: SIRPα-rituximab bispecific reagents bind to CD47 on the cell surface with reduced affinity relative to anti-CD47. The indicated antibodies were used to stain rat YB2/0 cells engineered to express human CD47, but not human CD20 (CD20−CD47+) prior to detection with fluorescently tagged anti-human secondary antibody by flow cytometry. 2B8=anti-CD20, B6H12=anti-CD47.
Figure 5B:
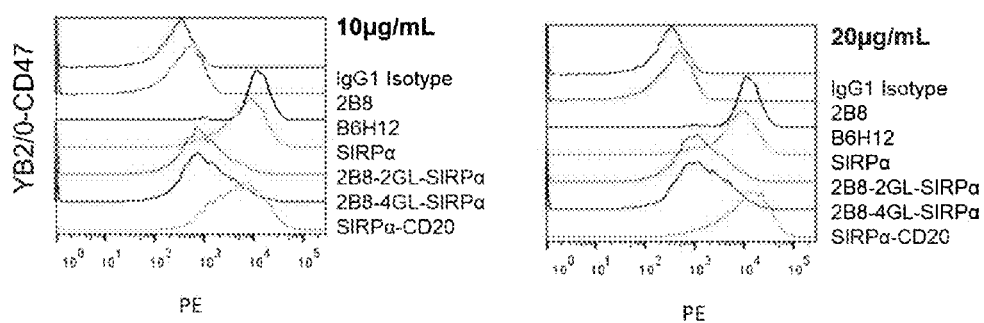

All SIRPabody reagents were able to bind to CD47, although the strength of binding varied between formats (FIG. 5).

Figure 6:
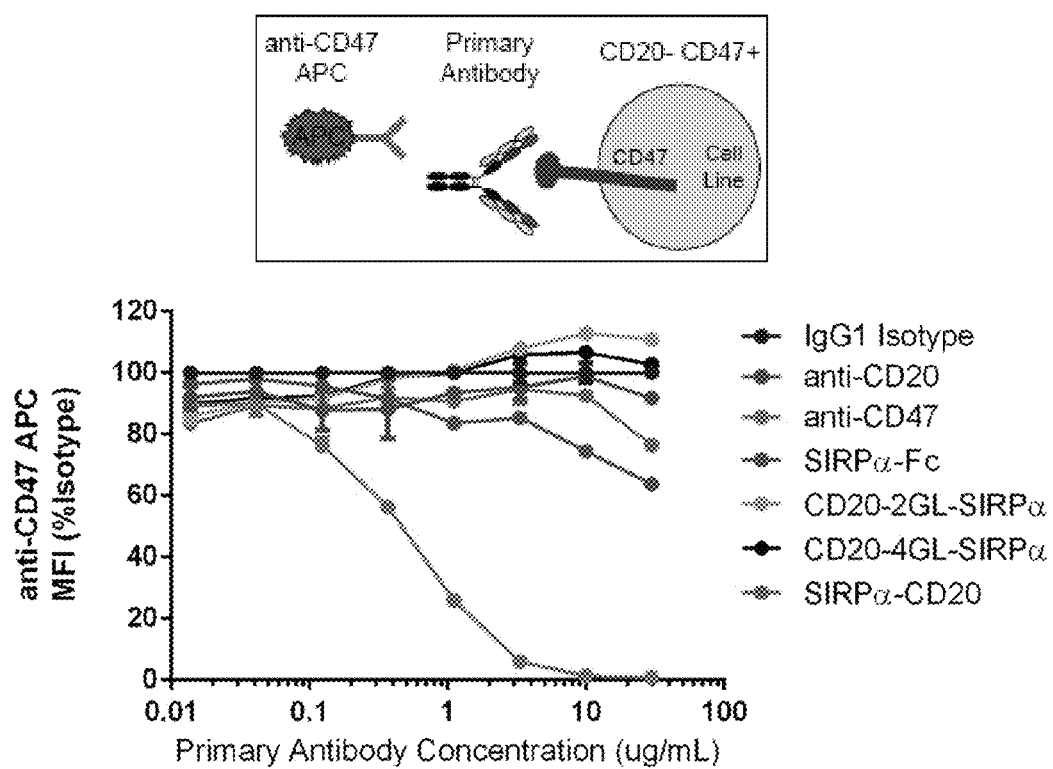
FIG. 6: Binding of SIRPα-rituximab bispecific reagents to CD47 is outcompeted by labeled anti-CD47. CD20−CD47+ YB2/0 cells were incubated with the indicated primary antibodies over a range of concentrations prior to staining with 10 μg/ml APC anti-CD47 and detection by flow cytometry. MFI of the APC signal for each condition is reported.

When CD47-expressing cells were first stained with SIRPabodies, subsequent incubation with labeled anti-CD47 outcompeted the primary SIRPabody staining, indicating a weak affinity of each SIRPabodies for CD47 (FIG. 6). Weak binding to CD47 is a desired characteristic for SIRPabodies, as those reagents will require the avidity contributions from interactions with CD20 for binding to dual antigen cells.

Figure 7:
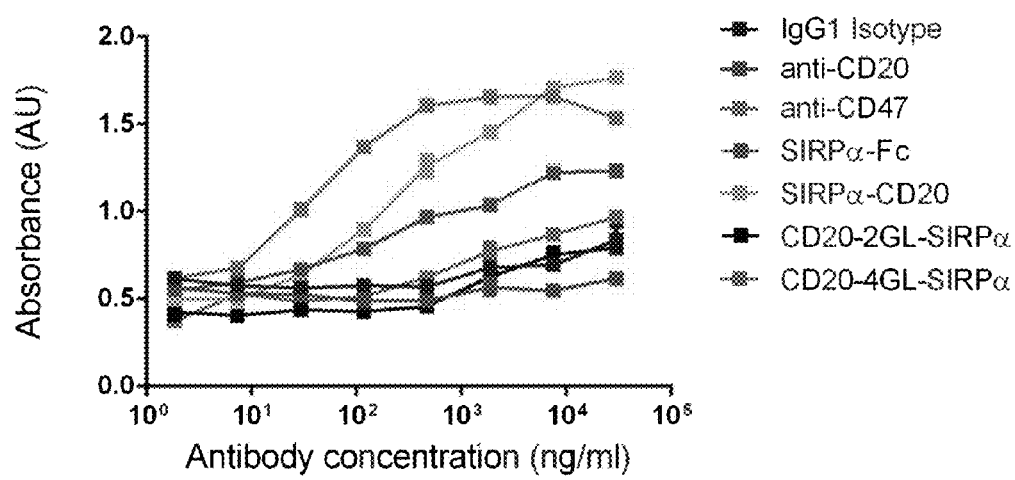
FIG. 7: SIRPα-rituximab bispecific reagents bind to CD47 with reduced affinity relative to anti-CD47 and other bispecific antibody formats. Binding of the indicated antibodies to the recombinant CD47 antigen was measured by ELISA over a range of concentrations. Immobilized human CD47 tagged with mouse Fc was used to capture the indicated antibodies prior to detection with HRP-conjugated antibody directed against the human kappa light chain. Data are representative of three experiments performed in triplicate.

To further explore the affinity of SIRPabodies to CD47, ELISA assays were performed to measure binding to recombinant CD47 antigen (FIG. 7). Consistently, all variants exhibited reduced affinity for CD47 relative to monoclonal anti-CD47. The affinity of each SIRPabody for CD47 was calculated using surface plasmon resonance measurements and relative affinities were consistent with all previous assays, indicating a reduced affinity for CD47 compared to monoclonal anti-CD47 (FIG. 8).

Figure 9:
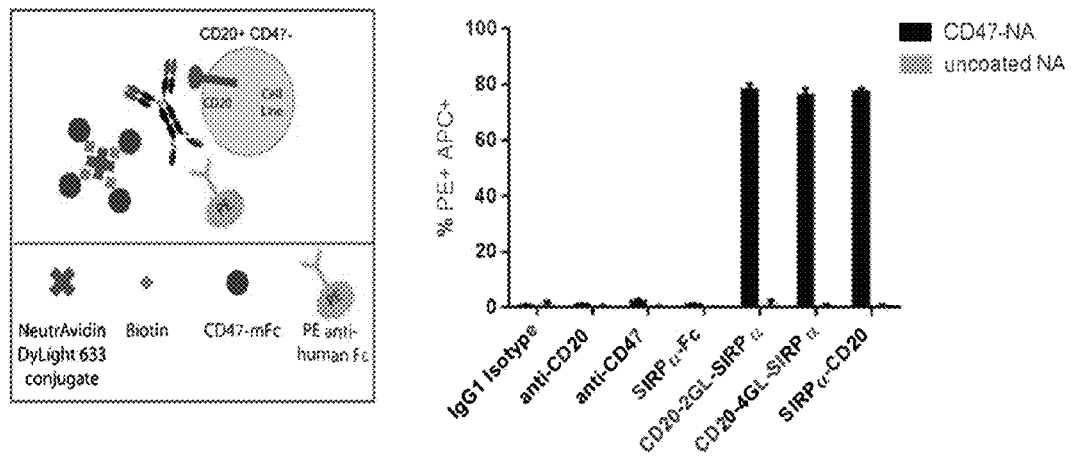
FIG. 9: SIRPα-rituximab bispecific reagents bind to CD20 and CD47 simultaneously. Schematic of assay to determine simultaneous binding to CD20 and CD47. Double positive events indicate simultaneous binding to CD20 and CD47 by the indicated antibodies.
Figure 10A:
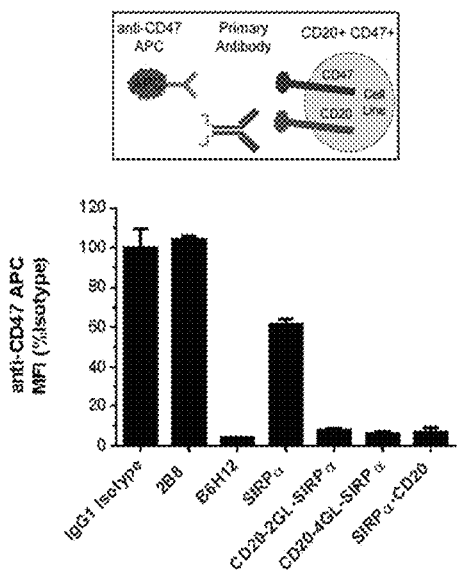
FIG. 10A-10B: SIRPα-rituximab bispecific reagents bind to CD20 and CD47 on dual antigen Raji cells. CD20+ CD47+ Raji cells were incubated with the indicated primary antibodies at 10 μg/ml prior to staining with APC anti-CD47 and detection by flow cytometry. CD20+CD47+ Raji cells were incubated with the indicated primary antibodies at 10 μg/ml prior to staining with DyLight 488anti-CD20 and detection by flow cytometry.
Figure 10B:
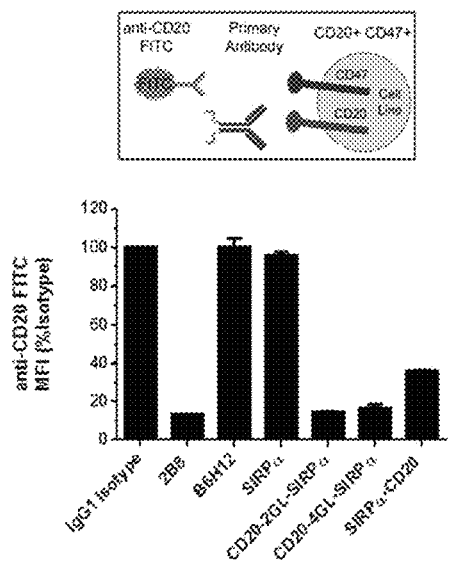

To assess whether SIRPabodies are capable of simultaneous binding to CD20 and CD47, antibodies were coincubated with CD20+CD47− cells and fluorescent NeutrAvidin coated with biotinylated CD47 fusion protein. SIRPabody binding was detected with secondary antibody and double positive fluorescent events indicated simultaneous binding to each antigen by the primary antibody (FIG. 9). Binding to both CD20 and CD47 on the cell surface was demonstrated by incubating cells expressing both antigens with SIRPabodies prior to staining with APC anti-CD47 or DyLight 488anti-CD20. All bispecific reagents blocked the subsequent binding of labeled antibody indicating binding to both antigens by the primary antibody stain (FIG. 10).

Figure 11A:
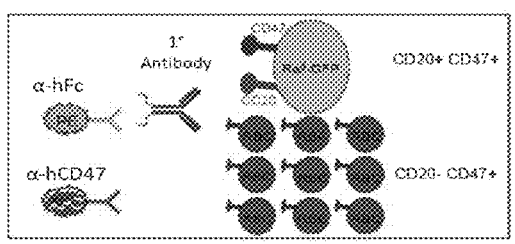
FIG. 11A-11D: SIRPα-rituximab bispecific reagents preferentially bind to dual antigen tumor cells in the presence of excess CD47-only expressing red blood cells.
Figure 11B:
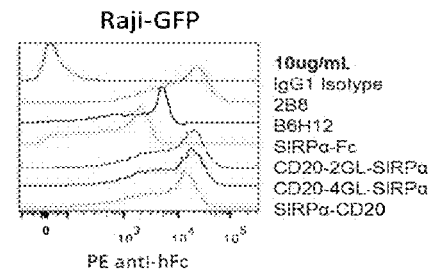
Figure 11C:
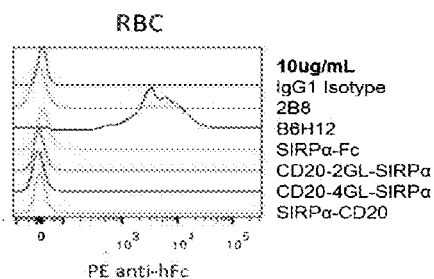
Figure 11D:
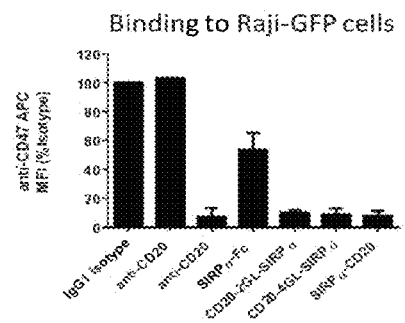

To determine whether the SIRPabodies have the desired selectivity for dual antigen cells in the presence of challenge with excess CD47-only expressing cells, CD20+CD47+ Raji cells were mixed with 20-fold excess red blood cells (RBCs) (CD47+CD20−). Cell mixtures were stained with SIRPabodies and antibody binding was detected with PE anti-human secondary (FIG. 11). All SIRPabodies bound to dual antigen tumor cells, while binding to single antigen RBCs was absent. Moreover, binding to dual antigen tumor cells was in part mediated by binding to CD47 as indicated by the ability of primary antibody stain to block subsequent staining with APC anti-CD47 (FIG. 11d).

Figure 12:
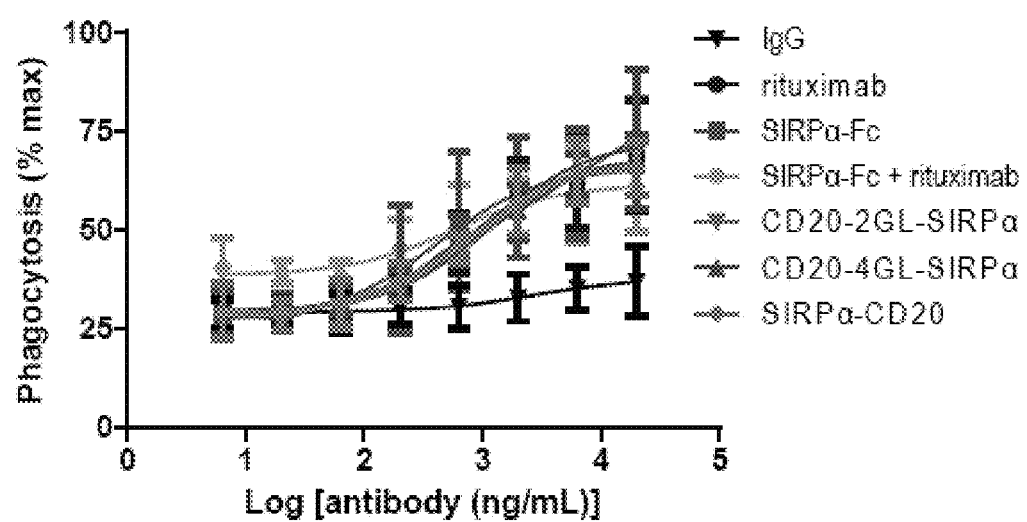
FIG. 12: SIRPα-rituximab bispecific reagents induce phagocytosis of dual antigen cells. Phagocytosis of CD20+ CD47+ Raji-GFP cells by human macrophages was assessed by flow cytometry. The percentage of GFP+ macrophages was normalized to the maximal response for each donor. Data averaged from 3 independent donors and are ±SD.
Figure 13A:
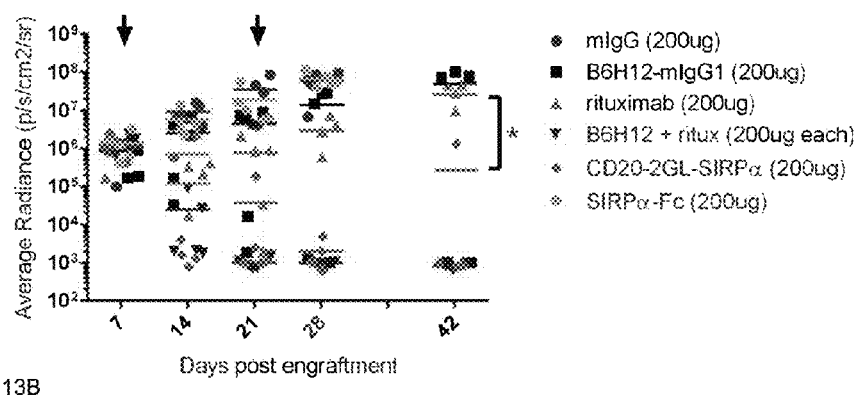
FIG. 13A-13B: CD20-2GL-SIRPα eliminates lymphoma in vivo.
Figure 13B:
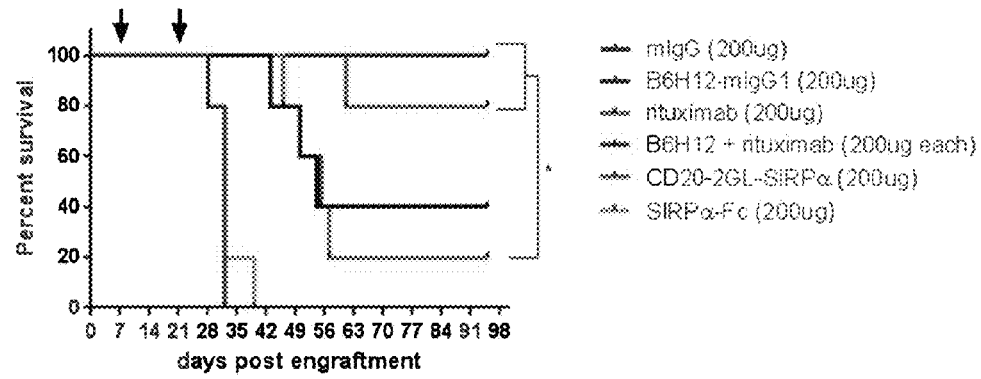
Figure 14A:
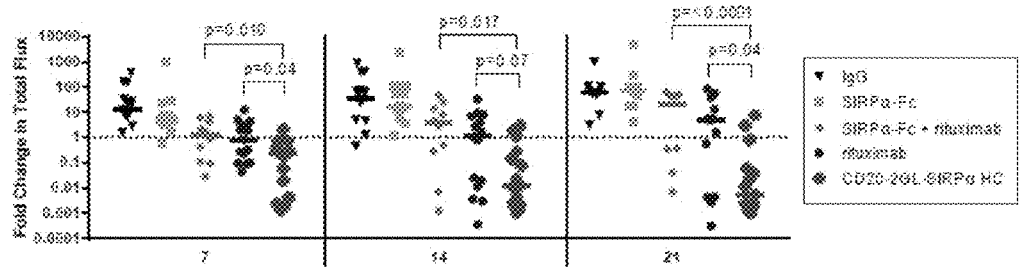
FIG. 14A-14D. CD20-2GL-SIRPα HC Reduces Lymphoma Burden and Extends Survival In Vivo.
Figure 14B:
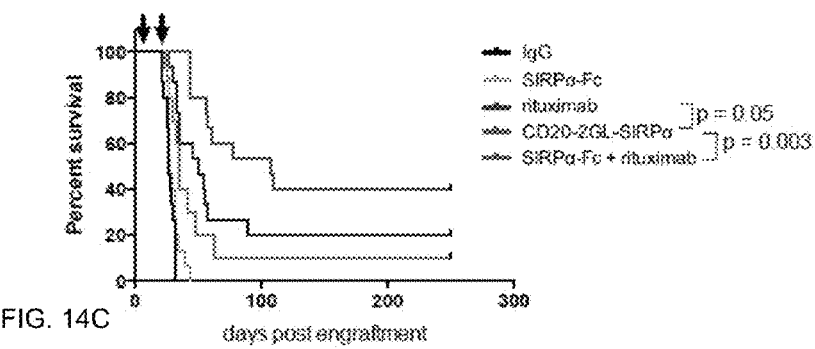
Figure 14C:
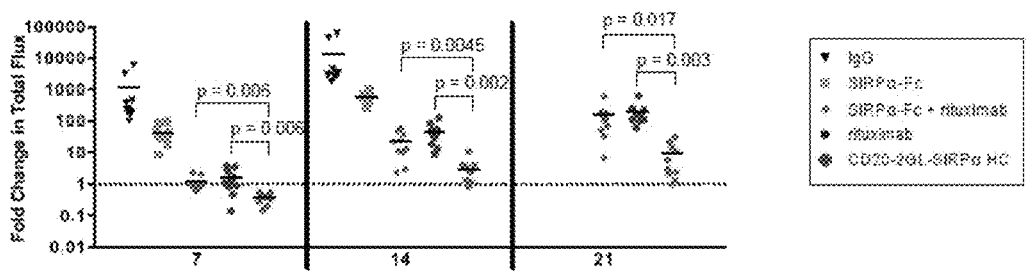
Figure 14D:
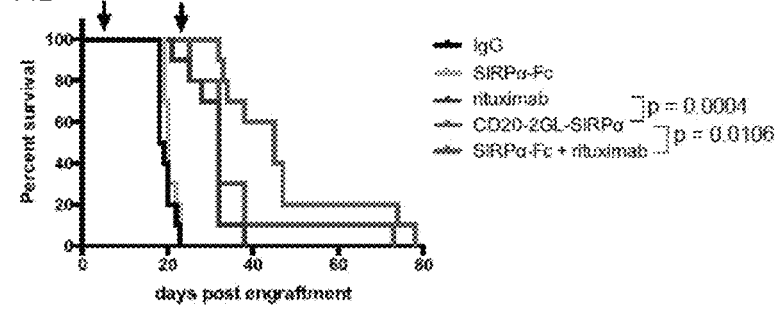

The therapeutic mechanism of action for SIRPabodies is induction of phagocytosis. Phagocytosis was measured in vitro by coincubating human macrophages with Raji-GFP cells in the presence of antibody. Engulfment of Raji cells by macrophages was detected by flow cytometry. All SIRPabodies were capable of inducing phagocytosis (FIG. 12).

CD20-2GL-SIRPα was selected as a lead candidate for further studies of therapeutic efficacy in vivo. A human lymphoma cell line engineered to express luciferase was engrafted subcutaneously into NSG mice to establish a model of localized lymphoma. Treatment with SIRPabody CD20-2GL-SIRPα resulted in elimination of the lymphoma and increased survival comparable to the synergistic effect seen with co-targeting CD20 and CD47 with combination antibody therapy.

Similar constructs were made for TIm3 and CD99. The sequence of an exemplary anti-CD99 light chain is provided in SEQ ID NO:12. The sequence of an exemplary anti-CD99 SIRPabody heavy chain is provided in SEQ ID NO:14, where the signal sequence is amino acid residues 1-19, the linker sequence is residues 471-480; and the SIRPα binding domain is residues 481-599.

What is claimed is:

1. A method of treating cancer, the method comprising administering an effective dose of a pharmaceutical composition comprising:
an effective dose of a SIRPabody polypeptide comprising an immunoglobulin variable region fused to a sequence an N-terminal Ig-like domain of Signal Recognition Protein alpha (SIRPα) wherein the domain of SIRPα is a polypeptide comprising the amino acid sequence of SEQ ID NO:1, to an individual in need thereof.

2. The method of claim 1, wherein the SIRPabody polypeptide comprises a first and a second polypeptide chain, which first polypeptide chain comprises (i) a first domain comprising a binding region of a light chain variable domain of an immunoglobulin ($V_L$) specific for a first epitope; and a second polypeptide comprising (i) a first domain comprising a binding region of a heavy chain variable region domain of an immunoglobulin ($V_H$) specific for the first epitope; and (ii) a second domain comprising the N-terminal Ig-like domain of SIRPα.

3. The method of claim 1, wherein the SIRPabody polypeptide comprises a first and a second polypeptide chain, which first polypeptide chain comprises (i) a first domain comprising a binding region of a light chain variable domain of an immunoglobulin ($V_L$) specific for a first epitope; and (ii) a second domain comprising the N-terminal Ig-like domain of SIRPα; and a second polypeptide comprising (i) a first domain comprising a binding region of a heavy chain variable region domain of an immunoglobulin ($V_H$) specific for the first epitope.

4. The method of claim 2 or claim 3, wherein the first polypeptide chain and the second polypeptide chain further comprise respective immunoglobulin heavy and light chain constant region domains.

5. The method of claim 2 or claim 3, wherein the first or the second polypeptide chain comprises the N-terminal Ig-like domain of SIRPα fused to the amino terminus of the $V_L$ or $V_H$ domain, respectively.

6. The method of claim 2 or claim 3, wherein the first or the second polypeptide chain comprises the N-terminal Ig-like domain of SIRPα fused to the carboxy terminus of the $C_L$ or $C_H$ domains, respectively.

7. The method of claim 2 or claim 3, wherein the SIRPα domain and the $V_H$ or $C_H$ domain are separated by a polypeptide linker of 1-20 amino acids in length.

8. The method of claim 1, wherein the the immunoglobulin variable region specifically binds a tumor antigen.

9. The method of claim 8, wherein the tumor antigen is CD20.

10. The method of claim 8, wherein the tumor antigen is TIM3.

11. The method of claim 8, wherein the tumor antigen is CD99.

12. The method of claim 1, wherein the cancer is a lymphoma or leukemia.

13. The method of claim 12, wherein the cancer is a Non-Hodgkin's B cell lymphoma.

14. The method of claim 12, wherein the cancer is chronic lymphocytic leukemia.

15. The method of claim 12, wherein the cancer is acute myeloid leukemia.

* * * * *